(12) United States Patent
Bae et al.

(10) Patent No.: US 7,659,314 B2
(45) Date of Patent: *Feb. 9, 2010

(54) PH-SENSITIVE POLYMERIC MICELLES FOR DRUG DELIVERY

(75) Inventors: You Han Bae, Salt Lake City, UT (US); Kun Na, Salt Lake City, UT (US); Eun Seong Lee, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 827 days.

This patent is subject to a terminal disclaimer.

(21) Appl. No.: 10/846,487

(22) Filed: May 14, 2004

(65) Prior Publication Data

US 2005/0186263 A1  Aug. 25, 2005

Related U.S. Application Data

(63) Continuation-in-part of application No. 10/640,739, filed on May 19, 2003, now Pat. No. 7,299,973.

(60) Provisional application No. 60/381,970, filed on May 19, 2002.

(51) Int. Cl.
*A61K 47/00* (2006.01)
*A61K 9/00* (2006.01)
*A01K 25/00* (2006.01)

(52) U.S. Cl. ............... 514/772.1; 424/400; 514/772
(58) Field of Classification Search .......... 514/772, 514/34; 424/400

See application file for complete search history.

(56) References Cited

U.S. PATENT DOCUMENTS 6,410,057 B1 * 6/2002 Kweon-Choi et al. ....... 424/501

OTHER PUBLICATIONS

Valero et al. Phase II study of liposome-encapsulated doxorubicin, cyclophosphamide, and fluolouracil as first-line therapy in paients with metastatic breast cancer. in Journal of Clinical Oncology 1999 17:1425-1434.*
Wang et al. Folate-mediated targeting of antineoplastic drugs, imaging agnets, and nucleic acid to cancer cells. Journal of Controlled Release 1998 53:39-48.*
Kwon et al. Polymeric micells as new drug cariers. Advanced Drug Delivery Reviews 1996 21:107-116.*
Taillefer et al. Preparation and characterization of pH-responsive polymeric micelles for the delivery of photosensitizing anticancer drugs. Journal of Pharmaceutical Sciences 2000 89:52-62.*

(Continued)

*Primary Examiner*—M P Woodward
*Assistant Examiner*—Caralynne E Helm
(74) *Attorney, Agent, or Firm*—Clayton, Howarth & Cannon, P.C.

(57) ABSTRACT

Mixed micelles containing poly(L-histidine)-poly(ethylene glycol) block copolymer and poly(L-lactic acid)-poly(ethylene glycol) block copolymer are a pH-sensitive drug carrier that release the drug in an acidic microenvironment, but not in the blood. Since the microenvironment of solid tumors is acidic, these mixed micelles are useful for treating cancer, including those cancers exhibiting multidrug resistance. Targeting ligands, such as folate, can also be attached to the mixed micelles for enhancing drug delivery into cells. Methods of treating a warm-blooded animal with such a drug are disclosed.

21 Claims, 26 Drawing Sheets

OTHER PUBLICATIONS

Choi et al Novel macromollecular self-organization of poly(ethylene glycol)-block-poly(L-histidine):pH-induced formation of core-shell nanoparticles in aqueous media. Bulletin of the Korean Chemical Society 2001 22:261-262.*

Muggia et al. Phase II study of liposomal doxorubicin in refractory ovarian cancer:antitumor activity and toxicity modification by liposomal encapsulation. Journal of Clinical Oncology 1997 15:987-993.*

Kitano et al. Macromolecules 1991 24:42-46.*

Leroux et al. Journal of Controlled Release 2001 72:71-84.*

J.M. Benns et al. pH-Sensitive Cationic Polymer Gene Delivery Vehicle: N-Ac-poly(L-histidine)-graft-poly(L-lysine) Comb Shaped Polymer, 11 Bioconjugate Chem. 637-645 (2000).

J.N. Cha et al. Biomimetic synthesis of ordered silica structures mediated by block copolypeptides, 403 Nature 289-292 (2000).

M.P. McCurdie et al. Solid-State Complexes of Poly(L-Histidine) with Metal Chlorides from the First Row of the d-Block, 37 J. Polym. Science: Part B: Polymer Physics. 301-310 (1999).

P. Midoux et al. Efficient Gene Transfer by Histidylated Polylysine/pDNA Complexes, 10 Bioconjugate Chem. 406-411 (1999).

K. Na et al. Self-Assembled Hydrogel Nanoparticles Responsive to Tumor Extracellular pH from Pullulan Derivative/Sulfonamide Conjugate: Characterization, Aggregation, and Adriamycin Release in Vitro, 19 Pharmaceutical Research 681-688 (2002).

D. Putnam et al. Polymer-based gene delivery with low cytotoxicity by a unique balance of side-chain termini, 98 Proc. Nat'l Acad. Sci. 1200-1205 (2001).

C.Y. Wang et al. Polyhistidine Mediates an Acid-Dependent Fusion of Negatively Charged Liposomes, 23 Biochemistry 4409-4416 (1984).

Eun Seong Lee, Kun Na, You Han Bae, Doxorubicin loaded pH-sensitive micelles for reversal of resistant MCF-7 tumor, Journal of Controlled Release, 103 (2005) 405-418.

Eun Seong Lee, Hyun Joon Shin, Kun Na, You Han Bae, Poly (L-histidine)-PEG block copolymer micelles and pH-induced destabilization, Journal of Controlled Release, 90 (2003) 363-374.

Eun Seong Lee, Kun Na, You Han Bae, Polymeric micelle for tumor pH and folate-mediated targeting, Journal of Controlled Release, 91 (2003) 103-113.

* cited by examiner

PH-SENSITIVE POLYMERIC MICELLES FOR DRUG DELIVERY

CROSS-REFERENCE TO RELATED APPLICATIONS

This application is a continuation-in-part of U.S. application Ser. No. 10/640,739, filed May 19, 2003, which claims the benefit of U.S. Provisional Application No. 60/381,970, filed May 19, 2002, both of which are hereby incorporated by reference.

STATEMENT REGARDING FEDERALLY SPONSORED RESEARCH OR DEVELOPMENT

Not applicable.

BACKGROUND OF THE INVENTION

This invention relates to drug delivery. More particularly, this invention relates to polymeric micelles for targeted drug delivery, including drug delivery for treating cancer and bypassing multidrug resistance of cancer cells by taking advantage of tumor and endosomal pH.

Although important findings in scientific research and technological advances, such as long-circulating carriers, enhanced permeation and retention (EPR) effect, and receptor-mediated endocytosis, have been achieved in the last decades for effective solid tumor targeting, chemotherapy still faces a major challenge for improving specific drug accumulation in tumor sites. Z. Ning et al., Increased microvascular permeability contributes to preferential accumulation of stealth liposomes in tumor tissue, 53 Cancer Res. 3764-3770 (1993); S. M. Moghimi et al., Long-circulating and target-specific nanoparticles: Theory and practice, 53 Pharmacol. Rev. 283-318 (2001); D. Putnam & J. Kopecek, Polymer conjugates with anticancer activity, 122 Adv. Polymer. Sci. 57-123 (1995); D.C. Drummond et al., Optimizing liposomes for delivery of chemotherapeutic agents to solid tumors, 51 Pharmacol. Rev. 691-743 (1999); M. Yokoyama, Novel passive targetable drug delivery with polymeric micelles, in Biorelated Polymers and Gels 193-229 (T. Okano ed. 1998).

The tumor extracellular pH ($pH_e$) is a consistently distinguishing phenotype of most solid tumors from surrounding normal tissues. The measured pH values of most solid tumors in patients, using invasive microelectrodes, range from pH 5.7 to pH 7.8 with a mean value of 7.0. More than 80% of these measured values are below pH 7.2, while normal blood pH remains constant at pH 7.4. K. Engin et al., Extracellular pH distribution in human tumors, 11 Int. J. Hyperthermia 211-216 (1995); R. van Sluis et al., In vivo imaging of extracellular pH using $^1$H MRSI, 41 Magn. Reson. Med. 743-750 (1999); A. S. E. Ojugo et al., Measurement of the extracellular pH of solid tumors in mice by magnetic resonance spectroscopy: a comparison of exogenous $^{19}$F and $^{31}$P probes, 12 NMR Biomed. 495-504 (1999). The acidity of tumor interstitial fluid is mainly attributed, if not entirely, to the higher rate of aerobic and anaerobic glycolysis in cancer cells (proton production by lactate formation and ATP lysis) than normal cells. M. Stubbs et al., Causes and consequences of tumour acidity and implications for treatment, 6 Opinion 15-19 (2000). Such acidic extracellular pH has prompted researchers to attempt to establish pH-sensitive anticancer drug delivery systems, such as pH-sensitive liposomes. However, effective systems have not been achieved because of lack of proper pH-sensitive functional groups in the physiological pH range. O. V. Gerasimov et al., Cytosolic drug delivery using pH- and light-sensitive liposomes, 38 Adv. Drug Deliv. Rev. 317-338 (1999); 0. Meyer et al., Copolymers of N-isopropylacrylamide can trigger pH sensitivity to stable liposomes, 421 FEBS Lett. 61-64 (1998). Recently, water soluble polymers modified with sulfonamide self-assembled nanoparticles showed enhanced drug release, interaction with and internalization into cells at tumor pH. K. Na & Y. H. Bae, Self-assembled hydrogel nanoparticles responsive to tumor extracellular pH from pullulan derivative/sulfonamide conjugate: Characterization, aggregation and adriamycin release in vitro, 19 Pharm. Res. 681-688 (2002); S. K. Han, K. Na & Y. H. Bae, Sulfonamide based pH-sensitive polymeric micelles: physicochemical characteristics and pH-dependent aggregation, Colloids. Surf. A. Physicochem. Eng. Aspects 00 1-11 (2002); K. Na, E. S. Lee & Y. H Bae, Adriamycin loaded pullulan acetate/sulfonamide conjugate nanoparticles responding to tumor pH: pH-dependent cell interaction, internalization and cytotoxicity in vitro, 87 J. Contr. Release 3-13 (2003).

In view of the foregoing, it will be appreciated that providing a pH-dependent drug carrier that releases a drug in the acidic microenvironment of solid tumors while maintaining stability in the blood would be a significant advancement in the art.

BRIEF SUMMARY OF THE INVENTION

An illustrative embodiment of the present invention comprises mixed micelles comprising poly(L-histidine)-poly(ethylene glycol) block copolymer and poly(L-lactic acid)-poly(ethylene glycol) block copolymer. Illustratively, the poly(L-histidine) portion has a molecular weight of at least about 5,000, and the poly(ethylene glycol) portion has a molecular weight of at least about 2,000. These mixed micelles comprise a hydrophobic interior portion, which can receive a drug, such as a hydrophobic drug. Included among such hydrophobic drugs are anticancer drugs, such as adriamycin (doxorubicin). These mixed micelles are pH-sensitive in that they are stable in the microenvironment of the blood, but are unstable and release the drug in the acidic microenvironment of solid tumors.

The mixed micelles can comprise varying amounts of the poly(L-histidine)-poly(ethylene glycol) block copolymer and of the poly(L-lactic acid)-poly(ethylene glycol) block copolymer. Illustrative embodiments of the mixed micelles comprise about 60-90% by weight of poly(L-histidine)-poly(ethylene glycol) block copolymer and about 10-40% by weight of poly(L-lactic acid)-poly(ethylene glycol) block copolymer. A typical embodiment within this range would comprise about 75% by weight of poly(L-histidine)-poly(ethylene glycol) block copolymer and about 25% by weight of poly(L-lactic acid)-poly(ethylene glycol) block copolymer.

The poly(L-histidine)-poly(ethylene glycol) block copolymer and/or the poly(L-lactic acid)-poly(ethylene glycol) block copolymer can also comprise a folate residue for targeting drug delivery by folate-receptor mediated endocytosis.

Other illustrative embodiments of the present invention comprise compositions of matter comprising poly(L-histidine)-poly(ethylene glycol) block copolymer and poly(L-histidine)-poly(ethylene glycol) block copolymer-folate. Still other illustrative embodiments of the invention comprise intermediates useful in the synthesis of these block copolymer compositions, including $N^{\alpha}$-carbobenzoxy-L-histidine, $N^{\alpha}$-carbobenzoxy-$N^{im}$-dinitrophenyl-L-histidine, $N^{im}$-dinitrophenyl-L-histidine N-carboxyanhydride, and poly($N^{im}$-dinitrophenyl-L-histidine).

Another illustrative embodiment of the invention comprises a method of making an imidazole-protected L-histidine N-carboxyanhydride comprising:

(a) reacting L-histidine, which comprises an α-amino group and an imidazole group, with an amino-group protecting reagent, resulting in an α-amino-protected L-histidine;

(b) reacting the α-amino-protected L-histidine with an imidazole-protecting reagent, resulting in an α-amino-protected and imidazole-protected L-histidine; and (c) reacting the α-amino-protected and imidazole-protected L-histidine with an anhydride-forming reagent, resulting in the imidazole-protected L-histidine N-carboxyanhydride.

In certain illustrative embodiments, the amino-group protecting reagent comprises benzyl chloroformate and the α-amino-protected L-histidine comprises $N^{\alpha}$-carbobenzoxy-L-histidine. Further, the imidazole-protecting reagent can comprise 2,4-dinitrofluorobenzene, and the α-amino-protected and imidazole-protected L-histidine comprises $N^{\alpha}$-carbobenzoxy-$N^{im}$-dinitrophenyl-L-histidine. Further, an illustrative anhydride-forming reagent comprises thionyl chloride. Still further, the imidazole-protected L-histidine N-carboxyanhydride can comprise $N^{im}$-dinitrophenyl-L-histidine N-carboxyanhydride.

Yet another illustrative embodiment of the invention comprises a method of making $N^{im}$-dinitrophenyl-L-histidine N-carboxyanhydride comprising:

(a) reacting L-histidine with benzyl chloroformate, resulting in an $N^{\alpha}$-carbobenzoxy-L-histidine;

(b) reacting the $N^{\alpha}$-carbobenzoxy-L-histidine with 2,4-dinitrofluorobenzene, resulting in an $N^{\alpha}$-carbobenzoxy-$N^{im}$-dinitrophenyl-L-histidine; and (c) reacting the $N^{\alpha}$-carbobenzoxy-$N^{im}$-dinitrophenyl-L-histidine with thionyl chloride, resulting in the $N^{im}$-dinitrophenyl-L-histidine N-carboxyanhydride.

Still another illustrative embodiment of the invention comprises a method of making an imidazole-protected poly(L-histidine) comprising:

(a) reacting L-histidine, which comprises an α-amino group and an imidazole group, with an amino-group protecting reagent, resulting in an α-amino-protected L-histidine;

(b) reacting the α-amino-protected L-histidine with an imidazole-protecting reagent, resulting in an α-amino-protected and imidazole-protected L-histidine;

(c) reacting the α-amino-protected and imidazole-protected L-histidine with an anhydride-forming reagent, resulting in an imidazole-protected L-histidine N-carboxyanhydride; and (d) converting the imidazole-protected L-histidine N-carboxyanhydride to an acid addition salt thereof and then polymerizing the imidazole-protected L-histidine N-carboxyanhydride acid addition salt by ring-opening polymerization in the presence of an initiator to result in the imidazole-protected poly(L-histidine).

Another illustrative aspect of the invention comprises a method of making poly($N^{im}$-dinitrophenyl-L-histidine) comprising:

(a) reacting L-histidine with benzyl chloroformate, resulting in $N^{\alpha}$-carbobenzoxy-L-histidine;

(b) reacting the $N^{\alpha}$-carbobenzoxy-L-histidine with 2,4-dinitrofluorobenzene, resulting in N-carbobenzoxy-$N^{im}$-dinitrophenyl-L-histidine;

(c) reacting the N-carbobenzoxy-$N^{im}$-dinitrophenyl-L-histidine with thionyl chloride, resulting in an $N^{im}$-dinitrophenyl-L-histidine N-carboxyanhydride; and (d) converting the $N^{im}$-dinitrophenyl-L-histidine N-carboxyanhydride to $N^{im}$-dinitrophenyl-L-histidine N-carboxyanhydride hydrochloride and then polymerizing the $N^{im}$-dinitrophenyl-L-histidine N-carboxyanhydride hydrochloride by ring-opening polymerization in the presence of n-hexylamine or isopropylamine to result in the poly($N^{im}$-dinitrophenyl-L-histidine).

Yet another illustrative aspect of the invention comprises a method of making poly(L-histidine) comprising:

(a) polymerizing $N^{im}$-dinitrophenyl-L-histidine N-carboxyanhydride hydrochloride by ring-opening polymerization in the presence of an initiator to result in poly($N^{im}$-dinitrophenyl-L-histidine); and (b) deprotecting the poly($N^{im}$-dinitrophenyl-L-histidine) to result in poly(L-histidine).

Still another illustrative embodiment of the invention comprises a method of making a poly(L-histidine)-poly(ethylene glycol) block copolymer comprising:

(a) reacting monocarboxylic acid-poly(ethylene glycol), comprising a carboxylic acid group, with an activating reagent to result in an activated monocarboxylic acid-poly (ethylene glycol) wherein the carboxylic acid group is activated;

(b) reacting poly($N^{im}$-dinitrophenyl-L-histidine), comprising a terminal α-amino group, with the activated monocarboxylic acid-poly(ethylene glycol) such that an amide bond is formed between the terminal α-amino group of poly ($N^{im}$-dinitrophenyl-L-histidine) and the carboxylic group of activated monocarboxylic acid-poly(ethylene glycol), resulting in a poly($N^{im}$-dinitrophenyl-L-histidine)-poly(ethylene glycol) block copolymer; and (c) deprotecting the poly($N^{im}$-dinitrophenyl-L-histidine)-poly(ethylene glycol) block copolymer to result in the poly (L-histidine)-poly(ethylene glycol) block copolymer.

In this embodiment, an illustrative activating reagent comprises N-hydroxysuccinimide, and, in such case, the activated monocarboxylic acid-poly(ethylene glycol) comprises N-hydroxysuccinimide-poly(ethylene glycol).

Still another illustrative embodiment of the invention comprise a method of making poly(L-histidine)-poly(ethylene glycol) block copolymer-folate comprising:

(a) activating folic acid, which comprises a carboxyl group, to result in activated folic acid wherein the carboxyl group is activated;

(b) reacting poly($N^{im}$-dinitrophenyl-L-histidine)-poly (ethylene glycol) block copolymer, comprising a terminal hydroxyl group, with the activated folic acid such that an ester bond is formed between the terminal hydroxyl group of the poly($N^{im}$-dinitrophenyl-L-histidine)-poly(ethylene glycol) block copolymer and the carboxyl group of the activated folic acid, resulting in poly($N^{im}$-dinitrophenyl-L-histidine)-poly (ethylene glycol) block copolymer-folate; and (c) deprotecting the poly($N^{im}$-dinitrophenyl-L-histidine)-poly(ethylene glycol) block copolymer-folate to result in the poly(L-histidine)-poly(ethylene glycol) block copolymer-folate.

In such embodiment, the carboxyl group can be illustratively activated with N,N'-dicyclohexylcarbodiimide.

Another illustrative aspect of the invention comprises a method for treating a warm-blooded animal with a drug comprising:

(a) mixing the drug with a pH-sensitive mixed micelle composition comprising (i) poly(L-histidine)-poly(ethylene glycol) block copolymer and poly(L-lactic acid)-poly(ethylene glycol) block copolymer, (ii) poly(L-histidine)-poly(ethylene glycol) block copolymer-folate and poly(L-lactic acid)-poly(ethylene glycol) block copolymer, (iii) poly(L-histidine)-poly(ethylene glycol) block copolymer and poly (L-lactic acid)-poly(ethylene glycol) block copolymer-folate, or (iv) poly(L-histidine)-poly(ethylene glycol) block copolymer-folate and poly(L-lactic acid)-poly(ethylene glycol) block copolymer-folate, to result in drug-loaded mixed micelle composition; and (b) administering the drug-loaded mixed micelle composition to the animal such that the drug-loaded mixed micelle composition is systemically circulated in the animal, wherein the drug-loaded mixed micelle composition is stable in the blood and the drug is released from the drug-loaded mixed micelle composition in acidic microenvironments of solid tumors and endosomes.

Yet another illustrative aspect of the invention comprises a method for treating multidrug resistance in a warm-blooded animal comprising administering into the systemic circulation of the animal a drug-loaded mixed micelle composition comprising a mixture of a hydrophobic anticancer drug and pH-sensitive mixed micelles comprising (i) poly(L-histidine)-poly(ethylene glycol) block copolymer and poly(L-lactic acid)-poly(ethylene glycol) block copolymer, (ii) poly(L-histidine)-poly(ethylene glycol) block copolymer-folate and poly(L-lactic acid)-poly(ethylene glycol) block copolymer, (iii) poly(L-histidine)-poly(ethylene glycol) block copolymer and poly(L-lactic acid)-poly(ethylene glycol) block copolymer-folate, or (iv) poly(L-histidine)-poly(ethylene glycol) block copolymer-folate and poly(L-lactic acid)-poly(ethylene glycol) block copolymer-folate.

A still further illustrative embodiment of the present invention comprises a method for treating a warm-blooded animal with a drug comprising:

(a) mixing the drug with a pH-sensitive mixed micelle composition comprising (i) poly(L-histidine)-poly(ethylene glycol) block copolymer or poly(L-histidine)-poly(ethylene glycol) block copolymer-targeting moiety and (ii) an amphiphilic polymer or amphiphilic polymer-targeting moiety, to result in a drug-loaded mixed micelle composition; and (b) administering the drug-loaded mixed micelle composition to the animal such that the drug-loaded mixed micelle composition is systemically circulated in the animal, wherein the drug-loaded mixed micelle composition is stable in the blood and releases the drug in the acidic microenvironments of solid tumors and endosomes.

An illustrative targeting moiety according to the present invention comprises folate or any other targeting moiety known in the art. Illustrative amphiphilic polymers according to the present invention comprise poly(L-lactic acid)-poly(ethylene glycol) block copolymer, poly(DL-lactic-co-glycolic acid), and ABA block copolymers, such as poly(ethylene oxide)-poly(propylene oxide)-poly(ethylene oxide) block copolymer.

BRIEF DESCRIPTION OF THE SEVERAL VIEWS OF THE DRAWINGS

FIGS. 5A-B show the determination of the critical micelle concentration (CMC) from the fluorescence intensity ($I_1$) obtained after scanning ($\lambda_{emission}$=360-460 nm) at $\lambda_{excitation}$=339 nm with a pyrene concentration of 1×10-6 M in NaOH—Na2B4O7 buffer (pH 8.0), wherein FIG. 5A shows intensity as a function of wavelength for polyHis5K-b-PEG2K concentrations from 0.5 to 100 μg/mL, and FIG. 5B shows intensity as a function of log polymer concentration.

(FIG. 13A) 0 wt %; pH 8.0 (●); pH 7.4 (■); pH 7.2 (▲); pH 7.0 (▼); pH 6.8 (♦); pH 6.2 (□); pH 5.0 (△). (FIG. 13B) 0 wt % (●); 10 wt % (■); 25 wt % (▲); and 40 wt % (▼) after 24 h.

FIG. 20A shows flow cytometry studies of sensitive MCF-7 (thick solid line) and DOX-resistant MCF-7 (MCF-7/DOX$^R$) cells (thin solid line). FIG. 20B shows the cytotoxicity of free DOX against MCF-7 (closed circles) and MCF-7/DOX$^R$ (open circles) cells at pH 8.0 (●), pH 7.4 (■), and pH 6.8 (▲) (n=7).

DETAILED DESCRIPTION

Figure 1:
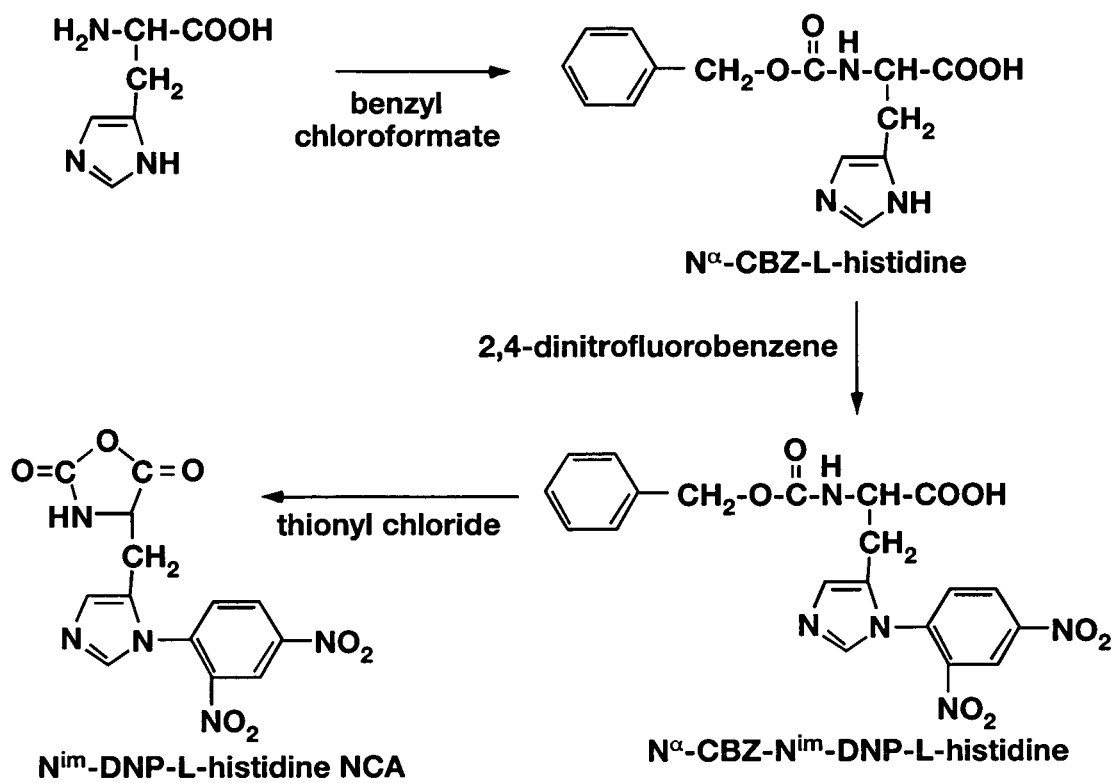
FIG. 1 shows a schematic representation of synthesis of protected L-histidine monomer according to the present invention.

Before the present compositions and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to a mixed micelle composition containing "a drug" includes a mixture of two or more drugs, reference to "an amino-group protecting reagent" includes reference to one or more of such reagents, and reference to "an initiator" includes reference to a mixture of two or more of such initiators.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "polyHis" means poly(L-histidine); "CBZ" means carbobenzoxy; "DNP" means dinitrophenyl; "NCA" means N-carboxyanhydride; "DP" means degree of polymerization; "M/I ratio" means monomer-to-initiator ratio; "NHS" means N-hydroxysuccinimide; "DCC" means N,N-dicyclohexylcarbodiimide; and "PEG" means poly(ethylene glycol). As used herein, "ADR" and "DOX" mean adriamycin or doxorubicin.

As used herein, "polyHis5K-b-PEG2K" means a block copolymer of polyHis and PEG wherein the polyHis portion has a molecular weight of about 5,000 and the PEG portion has a molecular weight of about 2,000.

As used herein, "administering" and similar terms mean delivering the composition to the individual being treated such that the composition is capable of being circulated systemically to the parts of the body, e.g., solid tumors, where the pH-sensitive mixed polymeric micelles encounter acidic conditions, relative to the blood, and release the drug. Thus, the composition is preferably administered to the individual by systemic administration, typically by subcutaneous, intramuscular, or intravenous administration, or intraperitoneal administration. Injectables for such use can be prepared in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added.

Illustrative anticancer drugs that may be administered according to the present invention include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene HCL, bleomycin sulfate, busulfan, buthionine sulfoximine, BWA 773U82, BW 502U83. HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride. Flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6, 4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

According to the present invention, one or more drugs, such as anticancer drugs, are incorporated into pH-sensitive mixed polymeric micelles, and then the drug-loaded pH-sensitive mixed polymeric micelles are administered to a warm-blooded animal, such as a human, such that the drug-loaded micelles enter into the systemic circulation of the animal. When the micelles encounter acidic conditions, such as the acidic microenvironment of solid tumors, the micelles release the drug. The released drug is then available to give its pharmacological effect.

According to the present invention, pH-sensitive mixed polymeric micelles comprise a mixture of poly(L-histidine)-poly(ethylene glycol) block copolymer and an amphiphilic polymer. These pH-sensitive mixed polymeric micelles are stable in the blood, but release a drug carried in such micelles upon encountering acidic conditions, such as the acidic microenvironments of solid tumors. Either or both of the poly(L-histidine)-poly(ethylene glycol) block copolymer and the amphiphilic polymer can be covalently coupled to a targeting moiety according to the present invention. The targeting moiety permits binding to receptors on the surfaces of cells. In one illustrative embodiment, folate is such a targeting moiety that has been covalently bonded to poly(L-histidine)-poly(ethylene glycol) block copolymer and to amphiphilic polymers. Other targeting moieties known in the art are also within the scope of the present invention. Amphiphilic polymers according to the present invention include poly(L-lactic acid)-poly(ethylene glycol) block copolymer, poly(DL-lactic-co-glycolic acid), and ABA block copolymers, such as poly(ethylene oxide)-poly(propylene oxide)-poly(ethylene oxide) block copolymer, and mixtures of any of the above.

Synthesis of Poly(L-histidine) and Block Copolymers

The imidazole ring has an electron lone pair on the unsaturated nitrogen that endows polyHis with an amphoteric nature by protonation-deprotonation. Its $pK_b$ value and pH-solubility dependence are influenced by the molecular weight (MW). D. W. Pack et al., Design of imidazole-containing endosomolytic biopolymers for gene delivery, 67 Biotech. Bioeng. 217-223 (2000); R. C. Bohinski, Modern Concepts in Biochemistry 4-24, 61 ($4^{th}$ ed. Allyn and Bacon: Boston, 1983). The polymer with a MW higher than 10,000 g/mole is water-soluble below pH 6.0 as a result of protonation. D. W. Pack et al., supra. In the protonated state, polyHis forms particles (120-200 nm) with anionic lipids, which demonstrated metal chelating properties. S. General & A. F. Thunemann, pH-sensitive nanoparticles of poly(amino acid) dodecanoate complexes, 230 Int'l J. Pharm. 11-24 (2001); M. P. McCurdie & L. A. Belfiore, Solid-state complexes of poly(L-histidine) with metal chlorides from the first row of the d-block, 37 J. Polym. Science: Part B: Polymer Physics. 301-310 (1999).

Recently, the probable fusogenic activity of polyHis, which disrupts the envelope membrane of acidic subcellular compartments such as endosomes and lysosomes, has drawn much attention for the design of non-viral gene delivery carriers. Plasmid DNA (pDNA) was incorporated into cationic polymeric carriers grafted with short polyHis side chains, P. Midoux & M. Monsigny, Efficient gene transfer by histidylated polylysine/pDNA complexes, 10 Bioconjugate Chem. 406-411 (1999); D. Putnam et al., Polymer-based gene delivery with low cytotoxicity by a unique balance of side-chain termini, 98 Proc. Nat'l Acad. Sci. USA 1200-1205 (2001); J. M. Benns, J. S. Choi, R. I. Mahato, J. S. Park, S. W. Kim, pH-sensitive cationic polymer gene delivery vehicle: N-Ac-poly(L-histidine)polyHis-graft-poly(L-lysine) comb shaped polymer, 11 Bioconjugate Chem. 637-645 (2000), and the resulting complex demonstrated an increase in gene transfection efficacy. This result was explained by assuming that the endosomal membrane had been disrupted by the proton-sponge effect of imidazole groups, facilitating the release of the DNA/polymer complex into the cytoplasm. In addition, polyHis has been shown to fuse with lipid bilayers upon protonation of imidazole groups as a result of interaction with negatively charged membrane phospholipids. C. Y. Wang & L. Huang, Polyhistidine mediates an acid dependent fusion of negatively charged liposomes, 23 Biochemistry 4409-4416 (1984). However, the use of polyHis as a gene carrier has been limited because polyHis does not form complexes with pDNA at neutral pH levels. Instead, poly(L-lysine) has been partially substituted with histidyl (or imidazole) residues. These histidylated poly(L-lysine)/pDNA complexes remarkably improve the transfection efficiency in vitro. P. Midoux & M. Monsigny, supra; D. Putnam et al., supra; J. M. Benns et al., supra.

Despite the potential of polyHis, its synthesis has restricted its application. The first synthetic method, ring-opening polymerization of $N^{im}$-benzyl-L-histidine N-carboxy-anhydride, was reported by A. Patchornik et al., poly-L-histidine, 79 J. Am. Chem. Soc. 5227-5230 (1957). However, difficulties in protecting the imidazole group by the formation of a stable L-histidine N-carboxyanhydride, and purifying N-carboxyanhydride, were serious problems. J. N. Cha et al., Biomimetic synthesis of ordered of silica structures mediated by block copolypeptides, 403 Nature 289-292 (2000); D. Poland & H. A. Scheraga, Theory of noncovalent structure in polyamino acids, in Poly-α-amino Acids 391-398 (Marcel Dekker, Inc., New York 1967). Since then, few papers on the synthesis of polyHis have been published, and methods for controlling the molecular weight (MW) of polyHis have not been available. However, a relatively higher molecular weight polyHis (up to 20,000 g/mole) has been commercialized. Recently, a few investigators have attempted to synthesize polyHis by peptide-synthesis methods, such as solid-phase (p-alkoxybenzyl alcohol resins) or liquid-phase (dimethylformamide) peptide synthesis, but the MW was relatively low, about 2,800 g/mole. D. Putnam et al., supra; J. S. Choi et al., Novel macromolecular self-organization of poly(ethylene glycol)-block-poly(L-histidine): pH-induced formation of core-shell nanoparticles in aqueous media, 22 Bull. Korean Chem. Soc. 261-262 (2001).

EXAMPLES 1-9

Examples 1-9 describe a method of making poly(L-histidine) ("polyHis") by ring-opening polymerization of L-histidine N-carboxyanhydride, the imidazole amine group of which was protected by a dinitrophenyl group. The synthesis of $N^{im}$-DNP-L-histidine NCA from L-histidine is summarized in FIG. 1, and the synthesis of polyHis from $N^{im}$-DNP-L-histidine NCA is summarized in FIG. 2. The resulting polyHis polymer (MW: 5,000 g/mole) was coupled to poly(ethylene glycol) (MW: 2,000 g/mole) via an amide linkage using the N,N'-dicyclohexyl carbodiimide (DCC) and N-hydroxysuccinimide (NHS)-mediated reaction. Poly(L-histidine)-poly(ethylene glycol) diblock copolymers (polyHis-b-PEG) were prepared and used for the construction of polymeric micelles responding to local pH changes in the body. The block copolymer in dimethylsulfoxide (DMSO) formed polymeric micelles on diafiltration against a borate buffer at pH 8. Dynamic light scattering (DLS) and atomic force microscopy (AFM) showed the micelles were spherical, having diameters of about 114 nm, with a unimodal distribution. The critical micelle concentration (CMC) at pH 8.0 was 2.3 mg/L. The CMC increased markedly on decreasing the pH of the diafiltration medium below pH 7.2. Micelles prepared at pH 8.0 were gradually destabilized below pH 7.4, as evidenced by a slight increase in light transmittance, an alteration in size distribution, and a decrease in the pyrene fluorescence intensity. Therefore, the ionization of the polyHis block forming the micelle core determined the pH-dependent CMC and stability.

EXAMPLE 1

Synthesis of $N^{\alpha}$-CBZ-L-histidine

L-Histidine monohydrochloride monohydrate (Sigma Chemical Co., Inc., St. Louis, Mo.) was purified by recrystallization from water/ethanol (7/3 v/v) at 0° C. The purified L-histidine monohydrochloride monohydrate (15 g) in ammonia water (28 wt %, 100 mL) was cooled to 0° C. Benzyl chloroformate (15 mL; Aldrich Chemical Co., Inc., Milwaukee, Wis.) was added dropwise to the solution while stirring continuously, which resulted in a white suspension. Stirring was continued for 1 h, followed by addition of an excess amount of diethyl ether (J. T. Baker, Deventer, Netherlands) to the reaction mixture and mixing for more 3 h. The impurities (excess benzyl chloroformate and by-products) were extracted twice with diethyl ether. Ammonia was removed from the aqueous phase, and the volume was increased to 100 ml with deionized water. After filtering, the filtrate was acidified by adding dilute sulfuric acid slowly with stirring until precipitation began. The isolated precipitate (mainly $N^{\alpha}$-CBZ-L-histidine), collected by filtration, was dissolved in acetic acid (50 mL) to remove any insoluble residuals. The product NO-CBZ-L-histidine was recrystallized from excess ethanol at 0° C., yield 62%. The product of this and other examples were analyzed using $^1$H NMR (300 MHz, 6 wt % sample solution) and by FT-IR (Perkin Elmer IR 2000, KBr pellet). $^1$H-NMR (D$_2$O, TMS): δ 8.09 (—N=CH—), δ 7.43 (protons on benzyl of CBZ), δ 6.05 ((—N—CH=C—), δ 5.41 (—COOCH$_2$—), d 4.52 (—CH—) and d 3.10 (—CH$_2$—).

EXAMPLE 2

Synthesis of $N^{\alpha}$-CBZ-$N^{im}$-DNP-L-histidine

A solution of Na-CBZ-L-histidine (7 g), prepared according to the procedure of Example 1, in distilled water (100 mL) containing sodium bicarbonate (8.4 g, to delay the reaction of 2,4-dinitrofluorobenzene with water; Sigma Chemical) and 0.5 M sodium hydroxide (NaOH, an activation agent) was cooled to 0° C. and 2,4-dinitrofluorobenzene (5 mL; Aldrich Chemical) in 1,4-dioxane (50 mL) was added. The reaction mixture was vigorously stirred at 0° C. for 8 h, then acidified with 3 N HCl aqueous solution to precipitate the product. The precipitate was filtered, washed with a small quantity of water and then with ethanol. After dissolving NW-CBZ-$N^{im}$-DNP-L-histidine in tetrahydrofuran (THF; Sigma Chemical), a 2-fold excess of petroleum ether (J.T. Baker) was added with stirring to reprecipitate Na-CBZ-$N^{im}$-DNP-L-histidine. The suspension was left undisturbed at 0° C. for one day, followed by filtration. This process was repeated. The final product was dried in vacuo for two days; yield 56%. $^1$H-NMR (DMSO-d$_6$ with TMS): δ 7.86-8.99 (protons on phenyl group, DNP), δ 8.05 (—N=CH—), δ 7.43 (protons on benzyl group, CBZ), δ 6.94 (—N—CH=C), d 5.41 (—COOCH$_2$—), d 4.52 (—CH—) and d 3.10 (—CH$_2$—).

EXAMPLE 3

Synthesis of $N^{im}$-DNP-L-histidine carboxyanhydride hydrochloride $N^{\alpha}$-CBZ-$N^{im}$-DNP-L-histidine (5 g), prepared according to the procedure of Example 2, was dried over phosphorus pentoxide in vacuo, dissolved in anhydrous THF (35 mL) and thionyl chloride (0.8 mL; Fluka, Buchs, Switzerland) was added. The mixture turned opaque and highly viscous. The reaction was allowed to occur at room temperature, resulting in a clear solution in a few minutes. After another 40 min, an excess of anhydrous diethyl ether (8-fold) was added to precipitate the product and the precipitate was filtered and dried in vacuo. To remove impurities, the product was dissolved in nitromethane (Aldrich Chemical) at room temperature and insoluble impurities removed by filtration. After stirring the solution in the presence of the activated carbon (dried in vacuo at 200° C. for three days), the solution was filtered three times to remove the activated carbon. $N^{im}$-DNP-L-histidine carboxyanhydride hydrochloride was crystallized by adding an 8-fold excess amount of anhydrous ethyl ether to the nitromethane solution. This process was repeated to obtain pure the pure N-carboxyanhydride (NCA). The crystals were filtered and dried for two days in vacuo in the presence of phosphorus pentoxide and NaOH powder; yield 67%. So-purified L-histidine-NCA was used for polymerization within 3 days. $^1$H-NMR (DMSO-$d_6$ with TMS): δ 7.86-8.99 (protons on phenyl group, DNP), δ 8.05 (—N=CH—), δ 7.10 (s; —NH), d 6.94 (—N—CH=C—), d 4.52 (—CH—), and d 3.10 (—CH$_2$—), respectively ; no CBZ group peak. FT-IR spectrum: 1780-1790 cm$^{-1}$ (N—C=O), 3340-3350 cm$^{-1}$ (NH)

EXAMPLE 4

Figure 2:
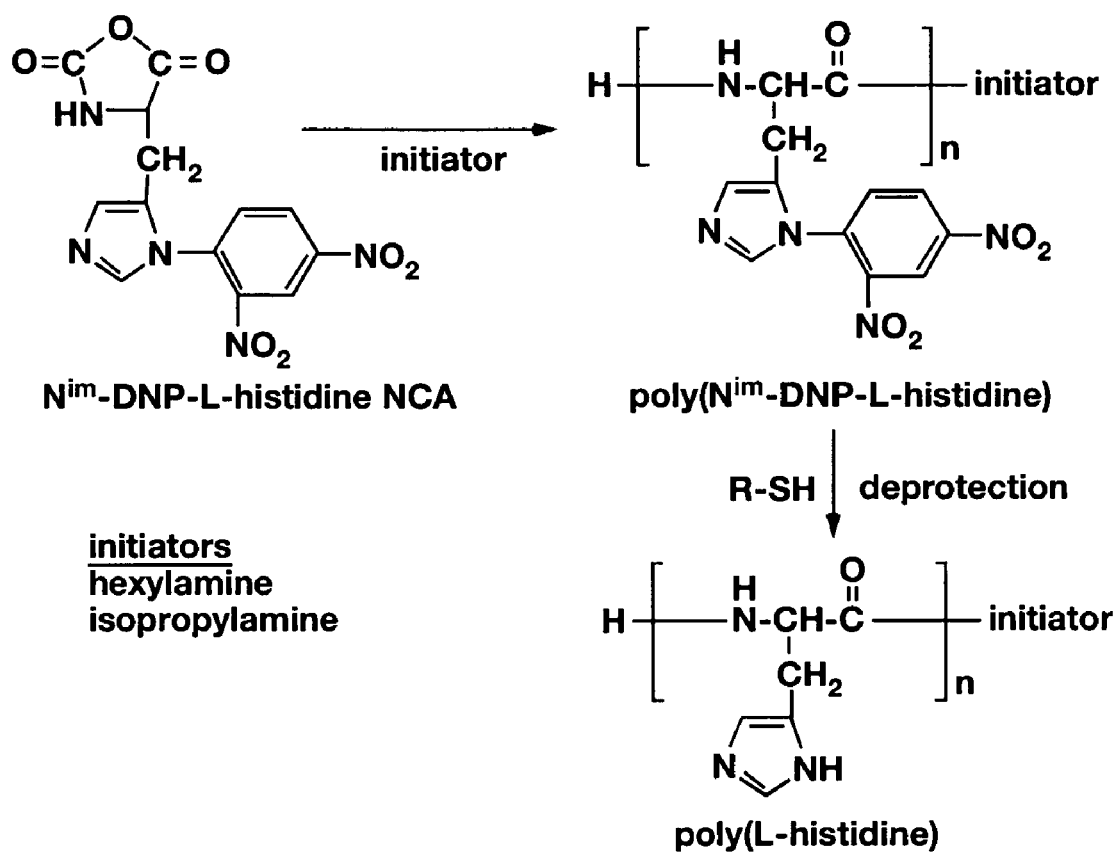
FIG. 2 shows a schematic representation of synthesis of poly(L-histidine) ("polyHis") according to the present invention.

Polymerization of $N^{im}$-DNP-L-histidine carboxyanhydride hydrochloride $N^{im}$-DNP-L-histidine NCA hydrochloride (1.4 g), prepared according to the procedure of Example 3, was dissolved in purified anhydrous dimethylformamide (DMF; J.T. Baker) (30 mL) and a predetermined amount of initiator (hexylamine or isopropylamine (Sigma Chemical) purified before use) was added to obtain different molecular weights of polymers. The polymerization proceeded at room temperature with evolution of carbon dioxide for 72 h (FIG. 2). An excess of 0.1 N HCl (600 mL) was added to precipitate poly($N^{im}$-DNP-L-histidine). After filtration, poly($N^{im}$-DNP-L-histidine) was dried in vacuo over phosphorus pentoxide for two days; yield 90%. The degree of polymerization (DP) of the polymers was estimated from the $^1$H-NMR spectrum (DMSO-$d_6$ with TMS) using the integration ratio of the peaks from the repeating unit (—CH—) and the initiator (—CCH$_3$). $^1$H-NMR spectrum: δ 7.86-8.99 (protons on phenyl group, DNP), δ 7.91 (—N=CH—), δ 6.94 (N—CH=C—), d 4.85 (—CH—), d 3.85 (—CH—NH$_2$), d 3.10-3.26 (—CH$_2$—) and d 1.06 (—CCH$_3$—).

$N^\alpha$-CBZ-$N^{im}$-DNP-L-histidine NCA.HCl was not soluble in most organic solvents used for the polymerization of amino acid NCAs, with the exception of DMF. The ring opening polymerization of Nu-CBZ-$N^{im}$-DNP-L-histidine NCA.HCl in DMF was performed using different molar ratios of the monomer to initiator (isopropylamine or n-hexylamine) (M/I ratio). Table 1 shows that the degree of polymerization (DP) of poly($N^{im}$-DNP-L-histidine) depended on the M/I ratio and the type of initiator. The DP of the polymer increased with increasing M/I ratio except for the high M/I ratios of 40:1 and 50:1. The primary amine as an initiator has higher reactivity with NCA than secondary or tertiary amine and induces faster initiation of polymerization. However, in this example high M/I ratios of 40:1 and 50:1 produced rather low molecular weight polymers. This observation is not well understood, but could be related to the diluted initiator concentration, which resulted in a longer time for polymerization, and to residual HCL salt in NCA. A molecule of L-histidine NCA has two nitrogens in the imidazole ring both of which are HCL salt-attachable, and the initiation may be influenced by the residual salts. A. Patchornik et al., supra; H. R. Kricheldorf, α-Aminoacid-N-carboxy-anhydrides and related heterocycles 93-95, 2 (Springer-Verlag Berlin Heidelberg New York 1987); W. N. E. Dijk-Wolthuis et al., Synthesis and characterization of poly-L-lysine with controlled low molecular weight, 198 Macromol. Chem. Phys. 3893-3906 (1997).

TABLE 1

Degree of polymerization of polyHis with M/I molar ratio and initiator (n = 5).

| Primary Initiator | M/I (N-carboxyanhydrides/Initiator) molar ratio | | | | |
|---|---|---|---|---|---|
| | 20/1 | 30/1 | 35/1 | 40/1 | 50/1 |
| n-Hexyl-amine | 16.2 ± 3.4 | 16.2 ± 3.4 | 28.3 ± 4.4 | 28.5 ± 3.5 | 12.3 ± 2.6 |
| Isopropyl-amine | 20.3 ± 3.3 | 32.4 ± 3.5 | 33.5 ± 3.6 | 24.5 ± 3.1 | 12.6 ± 2.9 |

For the M/I ratios of 20:1-35:1, almost all initiator molecules are expected to be incorporated into the growing chains. For n-hexylamine, the experimental DP was lower than the theoretical DP calculated from the M/I ratio. However, the DP of poly($N^{im}$-DNP-L-histidine) initiated by isopropylamine was close to the theoretical DP and slightly higher than theoretical expectation. This result is probably due to the relatively slower initiation and faster propagation rates by isopropylamine compared to n-hexylamine. H. R. Kricheldorf, supra. A slower initiation rate has often been observed in the case of secondary or tertiary amines that result in higher MW. A. Patchornik, supra; H. R. Kricheldorf, supra; W. N. E. Dijk-Wolthuis et al., supra. As shown in Table 1, the highest DP (33.5±3.6) of the polymer was obtained when the molar ratio of NCA to isopropylamine was 35:1.

EXAMPLE 5

Synthesis of poly($N^{im}$-DNP-L-histidine) and PEG block copolymer

Monocarboxylic acid-PEG was prepared as described in S. Zalipsky & G. Barany, Facile synthesis of α-hydroxy-ω-carboxymethylpolyethylene oxide, 5 J. Bioactive and Compatible Polymers 227-231 (1990). The preactivation of PEG (NHS-PEG) was performed with PEG (1 mole), NHS (1.5 moles), and DCC (1.25 moles) in methylene chloride (J.T. Baker) at room temperature. The coupling reaction between poly($N^{im}$-DNP-L-histidine) and NHS-PEG (1:1 functional group ratio) was carried out in THF for two days at room temperature. After reaction, the block copolymer was precipitated in a mixed solvent (THF/n-hexane) and filtered. The coupling of poly($N^{im}$-DNP-L-histidine) and PEG was confirmed by the transfer of peak at δ 3.85 (—CH—NH$_2$) to δ 4.85 (—CH—NH—CO—). The polymer was dried in vacuo for 2 days.

EXAMPLE 6

Deblocking of DNP Group

2-Mercaptoethanol (25 mL; Sigma Chemical) was added to the poly($N^{im}$-DNP-L-histidine)-PEG diblock copolymer (2 g), prepared according to the procedure of Example 5, in DMF (80 mL) (FIG. 2). Deprotection was complete within one day at room temperature. The solution was added to diethyl ether (800 mL) at 0° C. to precipitate polymer, while excess 2-mercaptoethanol and DNP-mercaptoethanol remained soluble. The polymer was filtered, washed with diethyl ether, and dried in vacuo for two days. For further purification, the polymer was dissolved in a minimum volume of 3 N HCl and stored in a 0° C. for one day. After precipitation of DNP was complete, the solution was filtered (0.45 μm) and the product was precipitated after adding excess acetone to the solution, and then dried in vacuo for 2 days. Dialysis (Spectra/Por; MWCO 5,000) was used to remove uncoupled polymers. Before subsequent experiments, the HCl salt of polyHis (1 mmole) in DMSO was converted to the free base by treatment with triethylamine (TEA; Sigma Chemical) (2 mmoles) for 3 h at room temperature; the free base was recrystallized from ethanol and dimethylsulfoxide (DMSO; J.T. Baker) (10:1).

The removal of DNP was confirmed by $^1$H-NMR (DMSO-$d_6$ with TMS): δ 7.90 (—N=CH—), δ 6.92 (N—CH=C), δ 4.85 (-CH—), δ 5.03 (OCH$_2$CONH, poly(ethylene glycol), δ 3.62-3.81 (protons on repeating units, poly(ethylene glycol), δ 3.10-3.26 (—CH$_2$—) and δ 1.06 (—CCH$_3$—). The diblock copolymers used for further micelle study were polyHis (MW: 5,000 g/mole)-block-poly(ethylene glycol) (MW: 2,000 g/mole) (denoted as polyHis5K-b-PEG2K) and polyHis (MW: 3,100 g/mole)-block-poly(ethylene glycol) (MW: 2,000 g/mole) (polyHis3K-b-PEG2K). The conjugation yields were 92 wt % and 86 wt %, respectively.

EXAMPLE 7

Titration of PolyHis-b-PEG Block Copolymers

The polymers and NaCl (control) were dissolved in 35 mL of deionized water (30 μmole/L) and the solution was adjusted to pH 12 with 1 M NaOH. The diluted solution was titrated by stepwise addition of 1 N HCL solution to obtain the titration profile. D. W. Urry et al., Comparison of electrostatic- and hydrophobic-induced pKa shifts in polypentapeptides. The lysine residue, 225 Chem. Phys. Lett. 97-103 (1994). The average value from triplicate titrations was plotted.

Figure 3A:
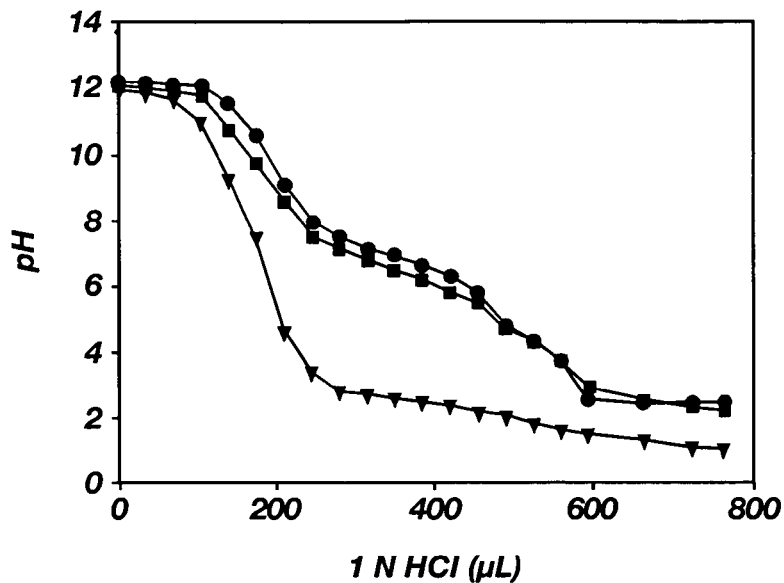
FIG. 3A shows the pH profiles by acid-base titration of polyHis5K-b-PEG2K (●), polyHis5K (■), and NaCl (▼).
Figure 3B:
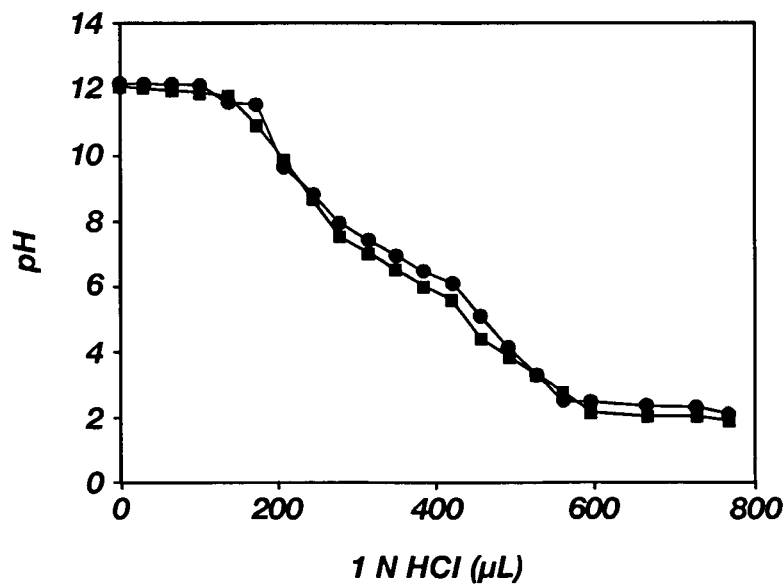
FIG. 3B shows the pH profiles by acid-base titration of polyHis3K-b-PEG2K (●) and polyHis3K (■).

It has been documented in literature that histidine residues in proteins significantly contribute to the protein buffering capacity at physiological pH level. A. Patchornik et al., supra. The acid-base titration profiles of the polyHis homopolymer and polyHis-b-PEG block copolymers are presented in FIG. 3. All of the polymer solutions exhibited a buffering pH region of pH 4-9. The titration curve confirmed that the polymers with a higher molecular weight polyHis block had a higher buffering capacity (FIG. 3A) in the physiological pH range of pH 5.5-8.0 due to the higher concentrations of imidazole rings. PolyHis5K-b-PEG2K and polyHis3K-b-PEG2K had inflexion points around pH 7.0 (pK$_b$). PolyHis5K and PolyHis3K showed pKb values around pH 6.5. The pK$_b$ shift of the block copolymer compared to the polyHis homopolymer may be due to increased hydration of the PEG. D. W. Urry et al., Comparison of electrostatic- and hydrophobic-induced pKa shifts in polypentapeptides. The lysine residue, 225 Chem. Phys. Lett. 97-103 (1994).

EXAMPLE 8

PolyHis-b-PEG Copolymer Micelles

Each polymer (20 mg) prepared according to the procedures of Examples 1-7 dissolved in DMSO (20 mL) was transferred to a pre-swollen dialysis membrane tube (Spectra/Por; MWCO 15,000) and dialyzed against HCl (or NaOH)—Na$_2$B$_4$O$_7$ buffer solution (pH 5.0-8.0, ionic strength=0.1) for 24 h. The outer phase was replaced with fresh buffer solution at 1, 2, 4, 6, and 10 h. The solution was subsequently lyophilized after filtering through a 0.8 μm syringe filter. The yield (wt %) of micelles was calculated by weighing the freeze-dried micelle powder.

The deprotonated polyHis at pH 8.0 is hydrophobic, while PEG is soluble in water at all pH's. This amphiphilicity at pH 8.0 was responsible for the formation of polymeric micelles. Lowering the solution pH below the pK$_b$ can affect the micellar structure because protonation converts the hydrophobic polyHis to a more hydrophilic block.

The polyHis-b-PEG block copolymer micelles were prepared by diafiltration of polymer solution in DMSO against a pH 8.0 medium. The yields (wt %) of micelle formation were 90-93 wt % for the block copolymer with polyHis5K and 28 wt % for polyHis3K-b-PEG2K.

Figure 4:
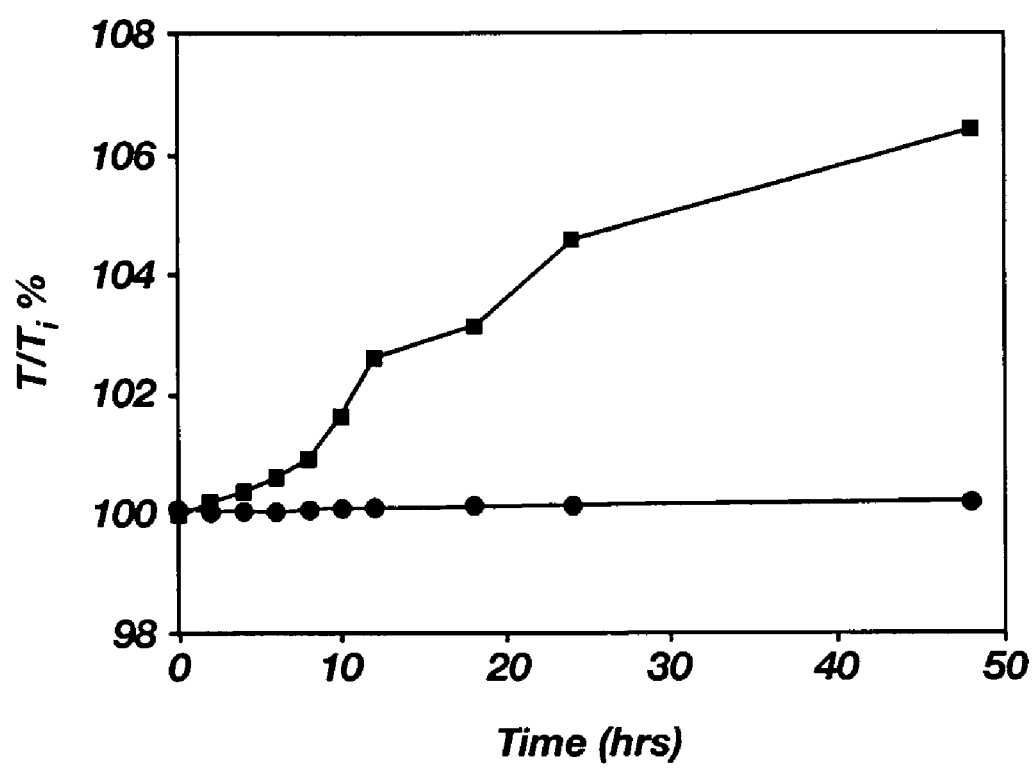
FIG. 4 shows the results of a stability study of micelles (0.1 g/L) at pH 8.0 through the change of transmittance at 37° C. $T/T_i$ is the transmittance at a given time divided by the transmittance at zero time: polyHis5K-b-PEG2K (●) and polyHis3K-b-PEG2K (■).

To evaluate the micellar stability, the time dependent turbidity change of each micelle was measured at pH 8.0 using a Varian CARY 1E UV/VIS spectrophotometer (FIG. 4). PolyHis3K-b-PEG2K micelles exhibited instability over time at pH 8.0 as shown by increasing light transmittance, while the stability of polyHis5K-b-PEG2K micelles at pH 8.0 was maintained for two days. The instability of polyHis3K-b-PEG2K at pH 8.0 was probably due to short polyHis block length and indicates that there may be a polyHis length somewhere between MW 3000 and MW 5000 at which stability increases.

Micelle formation was monitored by fluorometry in the presence of pyrene as a fluorescent probe. A stock solution of pyrene ($6.0 \times 10^{-2}$ M; Sigma Chemical) was prepared in acetone and stored at 5° C. until further use. For the measurement of steady-state fluorescence spectra, the pyrene solution in acetone was added to de-ionized water to give a pyrene concentration of $12.0 \times 10^{-7}$ M. The solution was then distilled under vacuum at 60° C. for 1 h to remove acetone from the solution. The acetone-free pyrene solution was mixed with the solution of polymeric micelles, the concentration of which ranged from $1 \times 10^{-4}$ to 1.0 g/L. For preparation of polymeric micelle solutions, a freeze-dried micelle sample was dispersed in HCl (or NaOH)—Na$_2$B$_4$O$_7$ buffer solution (pH 5.0-8.0, ionic strength=0.1). The initial pH of each micelle solution used for fluorescence study was tuned to the diafiltration pH used for micelle fabrication.

The final concentration of pyrene in each sample solution was $6.0 \times 10^{-7}$ M (its solubility limit in water at 22° C.). The pyrene emission at 339 nm was recorded. The CMC was estimated by plotting I$_1$ (intensity of first peak) of the emission spectra profile against of the log of the micelle concentration.

Figure 5A:
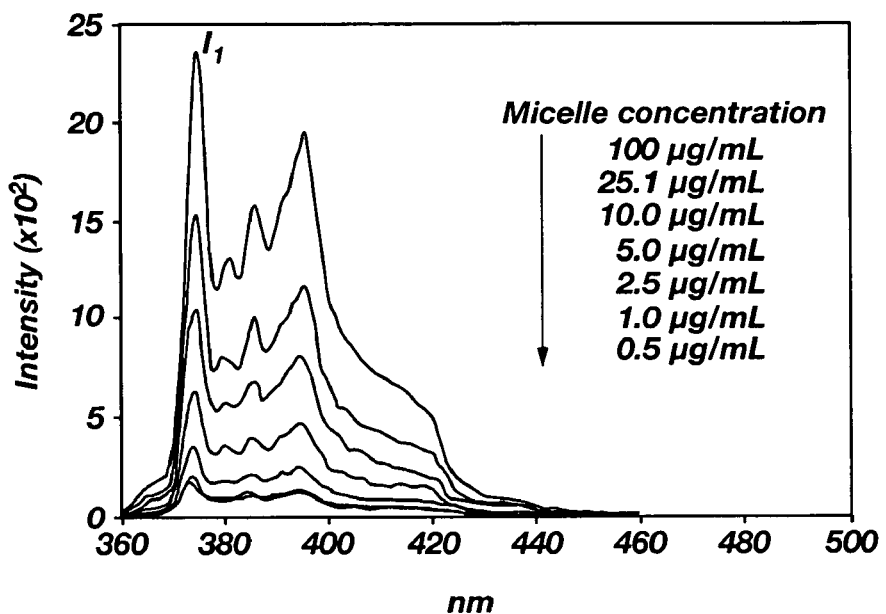
Figure 5B:
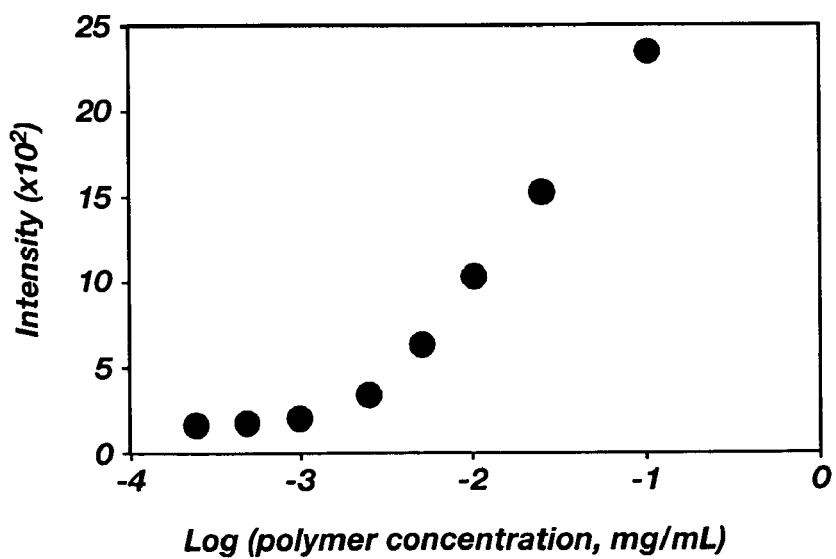

Pyrene strongly fluoresces in a non-polar environment, while in a polar environment it shows weak fluorescence intensity. The change of total emission intensity vs. polymer concentration indicates the formation of micelle or the change from micelle to unimer (dissociated polymer from disrupted micelle). C. M. Marques, Bunchy micelles, 13 Langmuir 1430-1433 (1997). FIG. 5A shows the change in intensity (I$_1$) of the first peak in the emission spectra plotted against polymer concentration. The CMC value was determined from the crossover point at low concentrations. The CMC of polyHis5K-b-PEG2K at pH 8.0 was 2.3 μg/mL (FIG. 5B) while that of polyHis3K-b-PEG2K was 62 μg/mL. This result supports the general propensity for a more hydrophobic block or a longer hydrophobic block to reduce the CMC.

Figure 6:
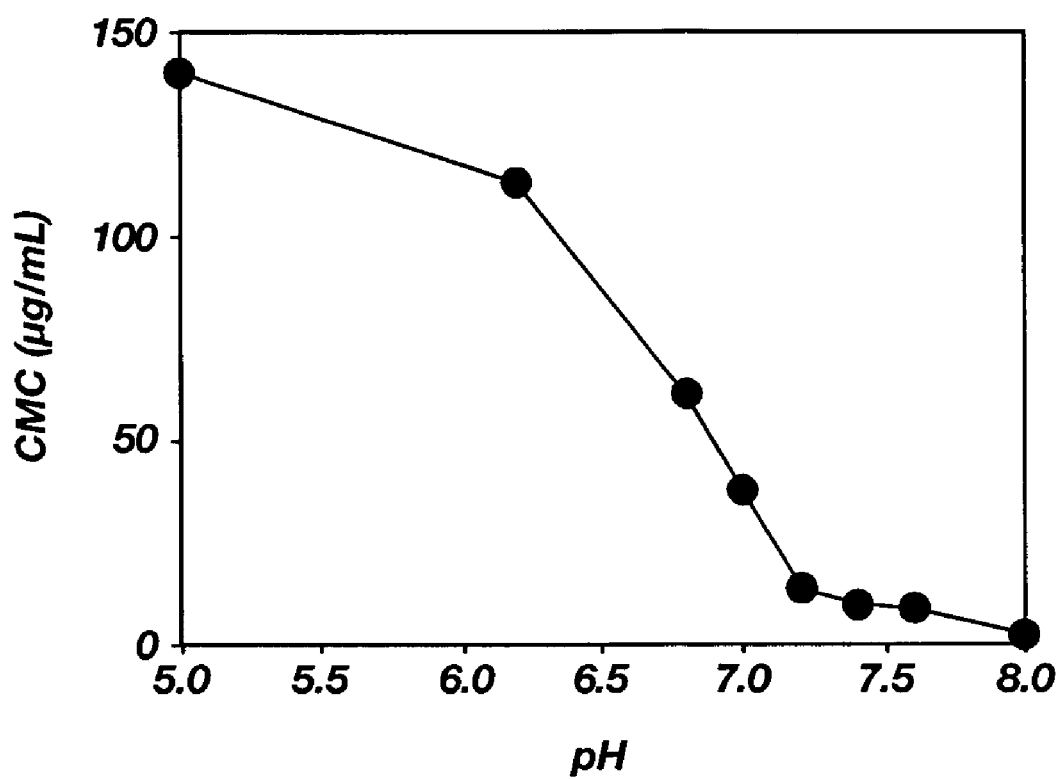
FIG. 6 shows the pH effect on the CMC of polyHis5K-b-PEG2K polymeric micelles that were prepared at various pHs from pH 5.0 to pH 8.0.

Since polyHis block is a polybase, the effect of the diafiltration pH on the CMC was examined and the results are presented in FIG. 6. At a diafiltration pH between 8.0 and 7.4, the CMC of polyHis5K-b-PEG2K micelle increased slightly with decreasing pH. However, the CMC was significantly elevated below pH 7.2. It is evident that the protonation of the imidazole group in the copolymer at lower pH level causes a reduction in hydrophobicity, leading to an increase in CMC. In addition, below pH 5.0 (typically pH 4.8), the CMC of polyHis5K-b-PEG2K micelle could not be detected. Taken together, at pH 8.0 the less protonated polyHis constitutes the hydrophobic core in the micellar structure, but in the range of pH 5.0-7.4 the polymer produced less stable micelles. This pH-dependent stability due to the protonation of the hydrophobic core is consistent with V. Biitiin et al., Unusual aggregation behavior of a novel tertiary amine methacrylate-based diblock copolymer: formation of micelles and reverse micelles in aqueous solution, 120 J. Am. Chem. Soc. 11818-11819 (1998). In the latter case, the "schizophrenic" AB block copolymers were composed of 2-(diethylamino)ethyl methacrylate (DEA) and 2-(N-morpholino)ethyl methacrylate (MEMA). The micelles from these block copolymers showed flip-flop self-assembly at pH 6.0-8.0, depending on the $pK_a$ value of each block. DEA-core micelles formed at pH 8.0 and disintegrated to unimers below pH 7.0, while MEMA-core micelles formed at pH 6.7 and reverted to unimers below pH 6.0.

Figure 7A:
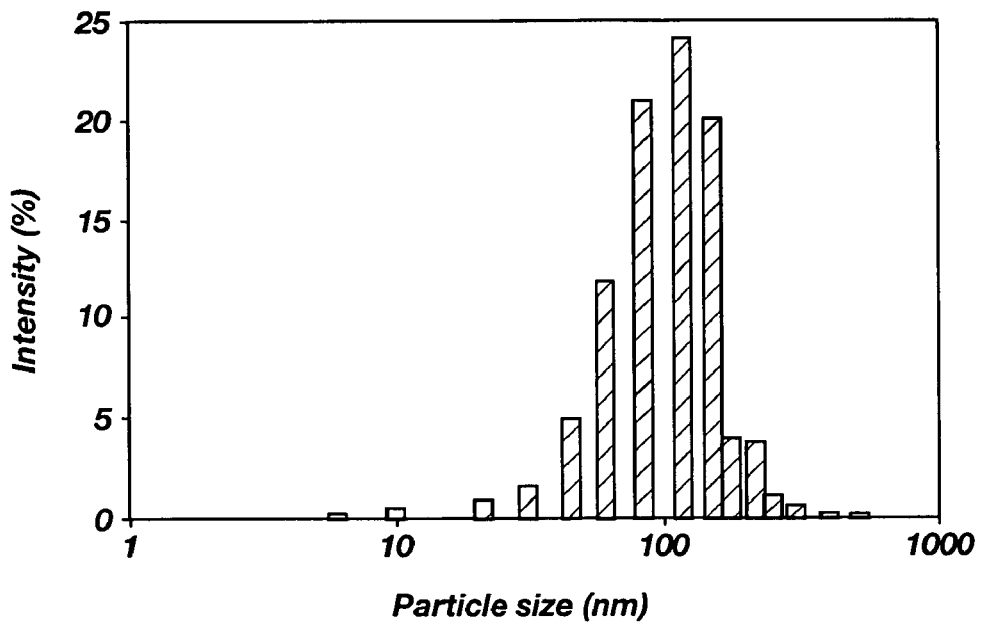
FIGS. 7A-B show the particle size distribution of polyHis5K-b-PEG2K polymeric micelles measured by dynamic light scattering (DLS) using a Zetasizer (FIG. 7A) and atomic force microscopy (AFM) (FIG. 7B).
Figure 7B:
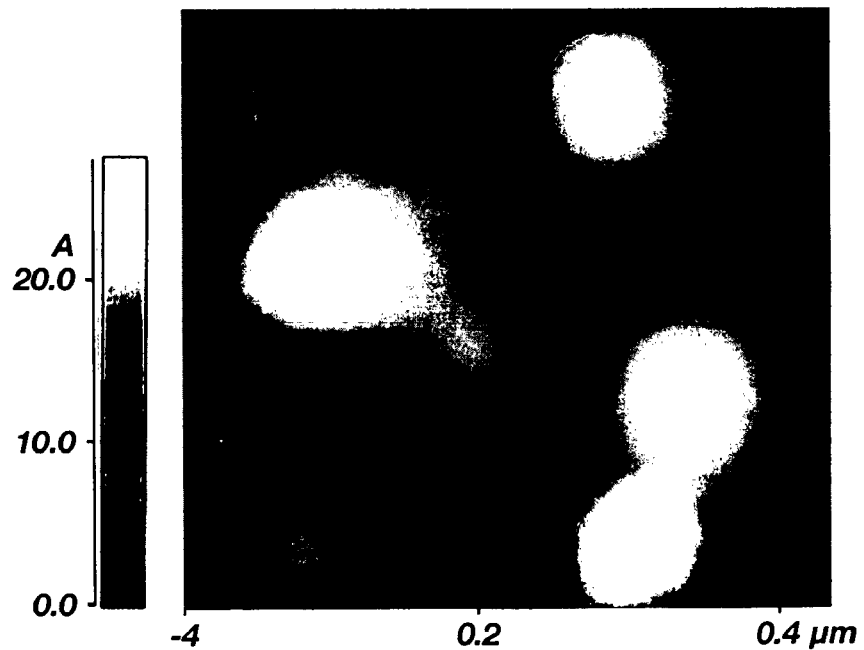
Figure 8:
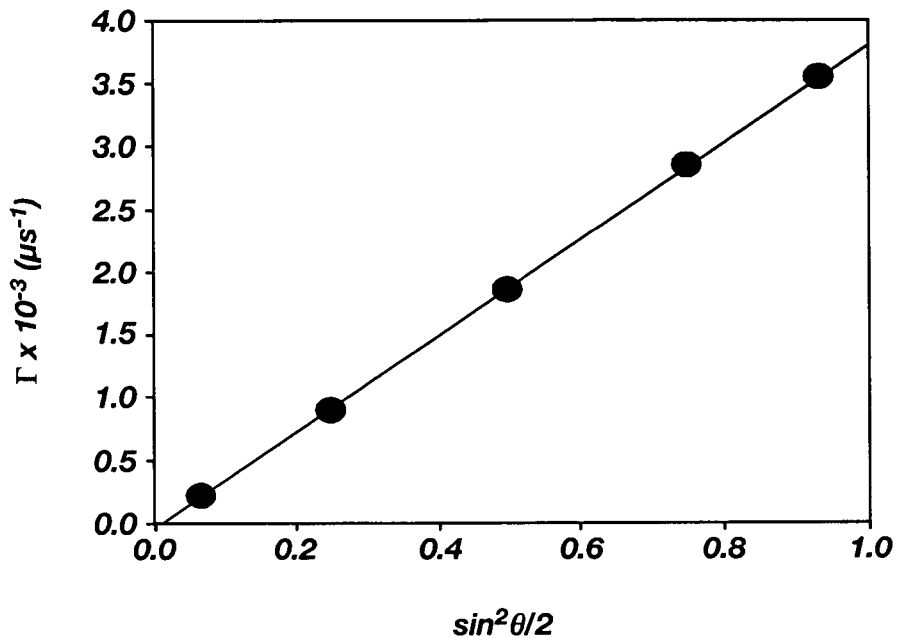
FIG. 8 shows the relaxation rate G of polyHis5K-b-PEG2K polymeric micelles as a function of $\sin^2(\theta/2)$ at room temperature.

The size of the micelles formed from polyHis5K-b-PEG2K was measured by photon correlation spectroscopy (PCS) using a Zetasizer 3000 (Malvern Instruments) with a He—Ne laser beam at a wavelength of 633 nm at 25° C. and a fixed scattering angle of 90°. The polymeric micelles (0.1 g/L) were exposed to different pH's for 24 h before measurement of the particle size and particle distribution. The particle size was 114 nm based on the intensity-average diameter with a unimodal distribution (FIG. 7A), and the ratio of weight average particle size to number average particle size was 1.2. The relatively large size of polyHis5K-b-PEG2K micelles may be the result of the diafiltration conditions. Kohori et al., Process design for efficient and controlled drug incorporation into polymeric micelle carrier system, 78 J. Control. Rel. 155-163 (2002), reported that the size of polymeric micelles composed of poly(N-isopropylacrylamide-co-N,N-dimethylacrylamide)-b-poly(DL-lactide) changed from 50 nm to 250 nm under different diafiltration conditions. The large size of polymeric micelles (over 100 nm) is most probably due to the formation of secondary aggregates that are clusters of individual single micelles. S. B. La et al., Preparation and characterization of the micelle-forming polymeric drug indomethacin-incorporated poly(ethylene oxide)-poly(beta-benzyl-L-aspartate) block copolymer micelle, 85 J. Pharm. Sci. 85-90 (1996). There is a probability that PolyHis5K-b-PEG2K micelles exist in a solution as secondary micelles. However, the polyHis5K-b-PEG2K micellar shape was regular and spherical as visualized by atomic force microscopy (AFM) (FIG. 7B). The AFM sample was prepared by casting a dilute micelle solution (10 mg/L, NaOH—Na$_2$B$_4$O$_7$ buffer solution, pH 8.0, ionic strength=0.1) on a glass slide, which was then dried in vacuo and observed by AFM (ThermoMicroscopes Explorer with ECU-plus electronics, Santa Clara, Calif.). The morphology of polymeric micelle was further evident from DSL measurements. DLS measurements were performed with an argon ion laser system adjusted to a wavelength of 488 nm. Each sample (0.1 g/L) was filtered through a 0.45-μm filter directly into a pre-cleaned 10 mm diameter cylindrical cell. The scattering angle was varied from 300 to 1500 and the temperature was controlled at 25° C. The particle diffusivity (or size) was calculated using the Stokes-Einstein equation, defined as $R_H=(k_B \times T)/(6 \times \pi \times \eta \times D_0)$, where $R_H$=hydrodynamic radius, $k_B$=Boltzmann constant, T=absolute temperature, η=solvent viscosity, $D_0$=diffusion coefficient at infinite dilution. The angular dependent diffusivity (or size) was obtained to estimate the micelle shape. FIG. 8 shows that the relaxation rates (r) were proportional to the square of the scattering vector (K=4pn$_0$ sin(q/2)/l$_0$), where there was n$_0$=solvent refractive index, l$_0$=wavelength, and q=scattering angle. Considering that the translational diffusion coefficient (D) of spherical particles is independent of detection angles, R. Xu et al., Light-scattering study of the association behavior of styrene-ethylene oxide block copolymers in aqueous solution, 24 Macromolecules 87-93 (1991), the D-values of particles can be calculated from the equation r=DK$^2$. R. Xu et al., supra; M. Iijima et al., Core-polymerized reactive micelles from heterotelechelic amphiphilic block copolymers, 32 Macromolecules 1140-1146 (1999). As shown in FIG. 8, D has no angular dependency and this confirms spherical micelles.

EXAMPLE 9 pH-Sensitivity of Micelles

The light transmittance of solutions was measured using a Varian CARY 1E UV/VIS spectrophotometer. pH was measured with a Fisher Accument Model 15 pH Meter. The pH-sensitivity was determined by measuring the pH-dependent light transmittance of the micellar solution, using a concentration of 0.1 g/L, initially at pH 8.0 (NaOH—Na$_2$B$_4$O$_7$ buffer solution, ionic strength=0.1). The pH was gradually decreased by adding 0.01 N HCl solution.

To verify the initial stability of micelles formulated at pH 8.0, the turbidity change of micelle solutions (0.1 g/L) at pH 8.0 (preparation pH) was determined from the light transmittance at λ=500 nm. The pH-dependent stability of micelles was measured by the transmittance change after the micelle samples were equilibrated with different pH buffer solutions (HCL or NaOH—Na$_2$B$_4$O$_7$ buffer, pH 6-8) for 24 h. The change in the pyrene fluorescence intensity of first peak (I$_1$) was measured after each sample was exposed to a different pH for 24 h.

Figure 9:
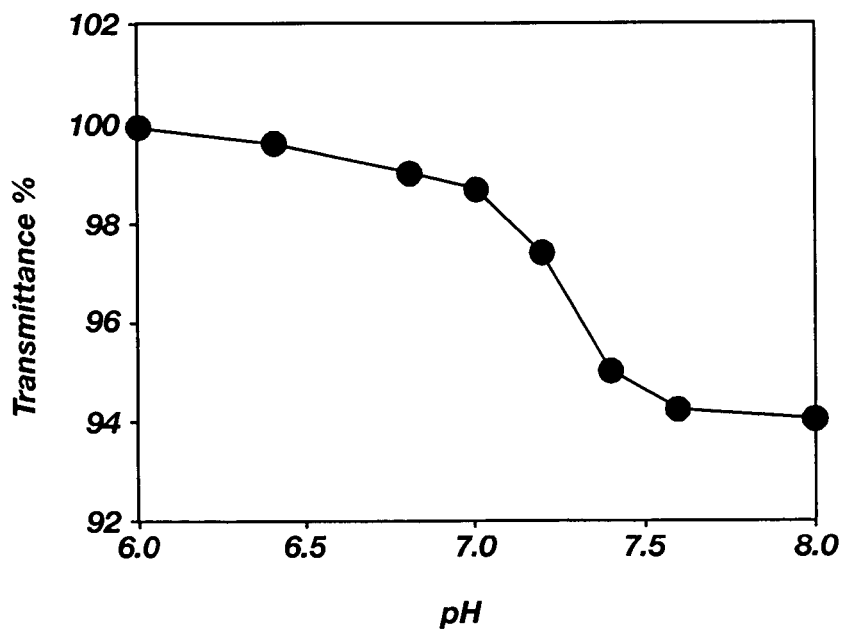
FIG. 9 shows the transmittance change of polyHis5K-b-PEG2K polymeric micelles (0.1 g/L) with pH. The polyHis5K-b-PEG2K polymeric micelles were prepared in NaOH—Na2B4O7 buffer (pH 8.0) and exposed at each pH for 24 h.

A noticeable increase in light scattering intensity was observed after dialyzing the block copolymer solutions at pH 8.0, while the unimer solution in DMSO was practically transparent. This indicates the formation of polymeric micelles after diafiltration. The micelle stability was confirmed by the measurement of transmittance of the micelle solution. FIG. 9 shows the transmittance change of the polymeric micelle solution as a function of pH. As the pH of the micelle solution decreased from the diafiltration conditions (pH 8, ionic strength 1.0), the transmittance increased. In particular, this increase was prominent from pH 7.4 to 6.0, reaching a plateau around pH 6.4. This result implies that polyHis5K-b-PEG2K micelles start dissociation from pH 7.4.

Figure 10:
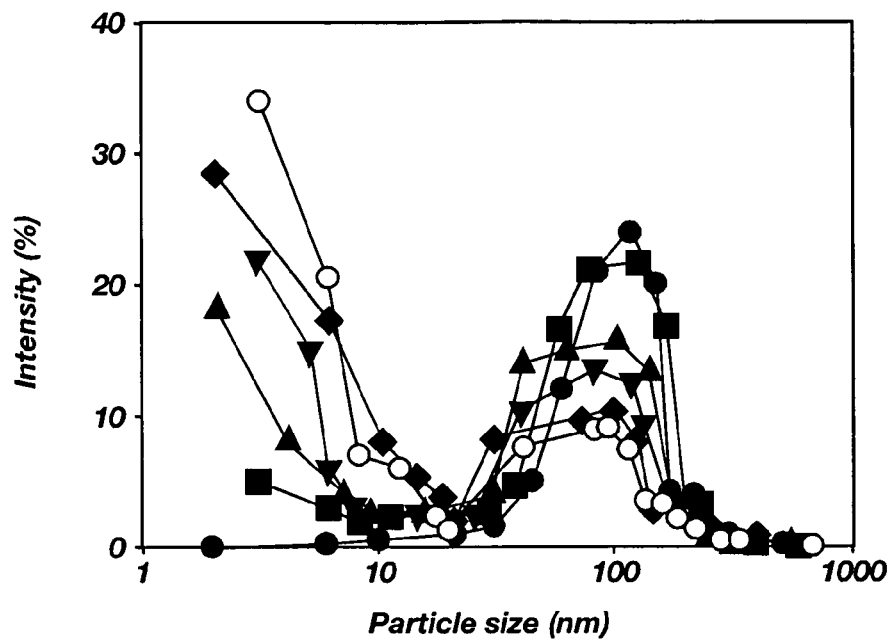
FIG. 10 shows the change of particle size distribution in polyHis5K-b-PEG2K micelles exposed to pH 8.0 (●), pH 7.4 (■), pH 7.2 (▲), pH 6.8 (▼), pH 6.4 (♦), or pH 6.0 (○) for 24 h.

FIG. 10 shows the changes in the particle size distribution of the micelles as a function of pH. The instability of the micelles on reduction of pH resulted in release of polyHis5K-b-PEG2K unimers that created a bimodal size distribution with existing micelles. The intensity of the peak at size 2-30 nm gradually increased with micelle disruption at a lower pH. Below pH 7.4, an abrupt increase in the intensity of small sized particles was apparent, which is consistent with the transmittance change of the micelle solution at this pH (FIG. 9).

Figure 11:
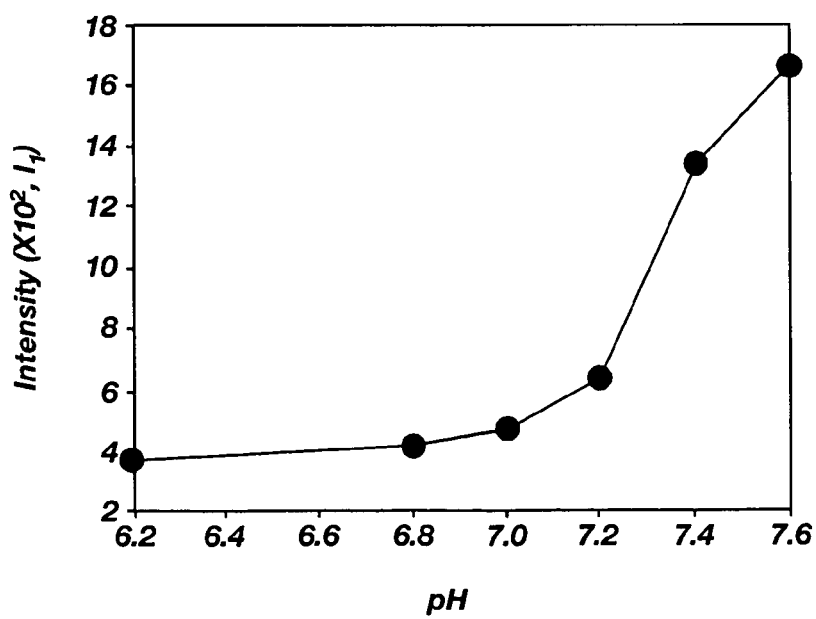
FIG. 11 shows the change of pyrene fluorescence intensity ($I_1$) with pH at constant micelle concentration (0.1 g/L). The polyHis5K-b-PEG2K polymeric micelles were prepared in NaOH (or HCl)—Na2B4O7 buffer (pH 8.0) and exposed to each pH for 24 h.

The micropolarity of pyrene as a function of pH was monitored to obtain a more detailed picture of the interior structural change of polymeric micelles. On reducing the solution pH, pyrene molecules in the polymeric micelles underwent a sharp increase in polarity, which was reflected by a decline in the fluorescence intensity of pyrene. FIG. 11 shows that the polyHis5K-b-PEG2K micelles prepared at pH 8.0 exhibit a sudden drop in fluorescence intensity at pH 7.0-7.4, followed by a gradual fall to a pH level of 6.0. It is apparent that this reduction of the fluorescence intensity was due to the instability of hydrophobic core and the cause of the dissociation of micelles is attributed to the protonation of the imidazole ring.

These pH-sensitive micelles will have wide utility in pharmaceutical applications, such as solid tumor treatment. For instance, the acidity of solid tumors is distinguishable from normal tissues. G. Kong et al., Hyperthermia enables tumor-specific nanoparticle delivery: effect of particle size, 60 Cancer Res. 4440-4445 (2000). The production of production of lactic acid under hypoxic conditions and the hydrolysis of ATP in an energy deficient environment are partially responsible for the acidic microenvironment of solid tumors. The blood pH is 7.4, while the extracellular pH ($pH_e$) of most solid tumors in patients measured by invasive microelectrodes ranged from pH 5.7 to pH 7.8, with a mean value of pH 7.0, wherein 80% of measured values are below pH 7.2. M. Stubbs et al., Causes and consequences of tumour acidity and implications for treatment, 6 Opinion 15-19 (2000).

Therefore, a polyHis5K-b-PEG2K block copolymer was synthesized and used to prepare pH-sensitive micelles. The critical micelle concentration was 2.3 mg/L at pH 8.0. The stability of the micelles depended on the hydrophobicity at a specified pH. The hydrophobic imidazole group in the histidine repeat unit becomes hydrophilic as a result of protonation of the amine group at lower pH. This pH sensitivity makes the micelles more effective for treating solid tumors by providing a switching mechanism for the release of drugs. Conventional pH-sensitive liposomes cannot distinguish differences in pH that are less than 1 pH unit. O. V. Gerasimov et al., Cytosolic drug delivery using pH- and light-sensitive liposomes, 38 Adv. Drug Deliv. Rev. 317-338 (1999). PolyHis5K-b-PEG2K micelles can provide the triggered release of an anticancer drug at tumor extracellular pH ($pH_e$, $\leq$pH 7.2) levels by physical destabilization of long-circulating polymeric micelles, G. Molineaux, Pegylation: engineering improved pharmaceuticals for enhanced therapy, Cancer Treat Rev. Suppl. A 13-16 (2002), to give higher local concentrations of the drug at tumor sites (targeted high-dose cancer therapy).

Mixed Polymeric Micelles

Polymeric micelles based on poly(L-histidine) (polyHis) as a pH-sensitive polybase, were further investigated as a pH-sensitive anticancer drug carrier. Here, polyHis was selected due to the multifunctionality to pH sensitivity, A. Patchornik et al., supra, biodegradability, and fusogenic activity, J. M. Benns et al., supra; D. Putnam et al., supra; C. Y. Wang & L. Huang, supra. The micelles were composed of polyHis/PEG and poly(L-lactic acid) (PLLA)/PEG block copolymer with or without folate conjugation, the folate conjugation aimed at folate-receptor-mediated endocytosis. S. D. Weitmann et al., Distribution of the folate receptor GP38 in normal and malignant cell lines and tissues, 52 Cancer Res. 3396-3401 (1992); J. F. Ross et al., Differential regulation of folate receptor isoforms in normal and malignant tissues in vivo and in established cell lines. Physiologic and clinical implications, 73 Cancer 2432-2443 (1994); P. S. Low & R. J. Lee, Folate-mediated tumor cell targeting of liposome-entrapped doxorubicin in vitro, 1233 Biochem. Biophys. Acta 134-144 (1995); J. A. Reddy & P. S. Low, Folate-mediated targeting of therapeutic and imaging agents to cancers, 15 Crit. Rev. Ther. Drug Carrier Syst. 587-627 (1998). The synthetic chemistry and physicochemical property of polyHis/PEG micelles were described in Examples 1-9.

EXAMPLES 10-15

Novel pH-sensitive polymeric mixed micelles composed of poly(L-histidine) (polyHis; MW 5,000)/PEG (MW 2,000) and poly(L-lactic acid) (PLLA) (MW 3,000)/PEG (MW 2,000) block copolymers with or without folate conjugation were prepared by diafiltration. The micelles were investigated for pH-dependent drug release, folate receptor mediated internalization and cytotoxicity with MCF-7 cells in vitro. The polyHis/PEG micelles showed accelerated adriamycin release as decreasing pH from 8.0. When the cumulative release for 24 hrs was plotted as a function of pH, the gradual transition in release rate appeared in a pH range from 8.0 to 6.8. To target triggering pH of polymeric micelles to more acidic tumor extracellular pH while improving the micelle stability at pH 7.4, PLLA/PEG block copolymer was blended with polyHis/PEG to form mixed micelles. This blending shifted the triggering pH to a lower value. Depending on the amount of PLLA/PEG, the mixed micelles were destabilized in the pH range of 7.2-6.6 (triggering pH for adriamycin release). When the mixed micelles were conjugated with folic acid, the in vitro results demonstrated that the micelles were more effective in tumor cell kill due to accelerated drug release and folate receptor-mediated tumor uptake. In addition, polyHis after internalization was proven to be effective for cytosolic ADR delivery by its fusogenic activity. This approach is expected to treat solid tumors in vivo.

EXAMPLE 10

Synthesis of Poly(L-lactide)/PEG Block Copolymers

PLLA(3K)/PEG(2K) diblock copolymer was prepared by a conventional method known in the art. S. K. Han, K. Na, Y. H. Bae, Sulfonamide based pH-sensitive polymeric micelles: physicochemical characteristics and ph-dependent aggregation, Colloids. Surf. A. Physicochem. Eng. Aspects 00 (2002) 1-11.

Example 11

Synthesis of poly(L-histidine)/PEG-folate

The carboxyl group of folic acid (3 mmol) dissolved in 50 mL DMSO was preactivated with DCC (1.2 mmol) at room temperature for 4 hours. Poly(L-$N^{im}$-DNP-His)/PEG-OH (1 mmol) and DMAP (a catalyst, 0.1 mmol) were added to the reactor and reacted with preactivated folic acid at room temperature overnight. After reaction, unreacted folic acid was removed by dialysis (MWCO 2,000). A yellow powder was obtained after freeze drying. Finally, poly($N^{im}$-DNP-His)/PEG-folate was then deprotected by thiolysis with 2-mercaptoethanol to yield polyHis (5K)/PEG (2K)-folate. The yield of this conjugate was 92%.

EXAMPLE 12

Synthesis of poly(L-lactic acid)/PEG-folate

For amination, folic acid (1 mmol) dissolved in 30 mL DMSO was reacted with DCC (1.2 mmol) and NHS (2 mmol) at 50° C. for 6 hours. The resulting folate-NHS was mixed with ethylene diamine (10 mmol) plus 500 mg pyridine and allowed to react at room temperature overnight. The reaction was confirmed by TLC analysis (silica gel plate, 2-propanol/ chloroform=70/30 vol %). The crude product was precipitated by addition of excess acetonitrile, filtered and washed three times with diethyl ether before drying under vacuum. For further purification, this product was dissolved in 2 N HCl and precipitated by adding excess 8-fold acetonitrile. After filtration, the fine dark yellow powder was dried in vacuo. The unreacted folic acid and diaminated folic acid (folate-$(NH_2)_2$) were separated by ion exchange chromatography. The column (10×100 mm) was packed by swollen DEAE Sephadex A-25 in 0.5 M potassium tetraborate solution. After the product (0.5 mg) dissolved in deionized water (20 mL) was loaded into the column, the linear ionic gradient of ammonium bicarbonate solution (10 to 30 mM) was applied. The folate-$NH_2$ solution was fractionally collected after continuous TLC analysis as mentioned above. The folate-$NH_2$ solution was evaporated, and then added NaCl to remove remaining ammonium bicarbonate. The final product was obtained from recrystallization (water/acetonitrile) and vacuum drying (yield=36%). PLLA/PEG-COOH (1 mmol) was activated using DCC (1.2 mmol) plus NHS (2 mmol) in methylene chloride. Dicyclohexylurea (DCU) was removed by filtration and excess diethyl ether added to the crude solution, and then PLLA/PEG-NHS was obtained from recrystallization. The activated PLLA/PEG-NHS (1 mmol) and aminated folate (2 mmol) were reacted in DMSO at room temperature for two days. The unreacted amine-folate was removed by dialysis (MWCO 2,000). The final yellowish product was obtained by freeze-drying. The yield of this conjugate was 91%.

EXAMPLE 13

Preparation of pH-sensitive Mixed Micelles

The pH-sensitive micelles were prepared with polyHis/PEG with or without folate and PLLA/PEG with or without folate. Before adriamycin (ADR) loading into the polymeric micelle, adriamycin hydrochloride (ADR-HCL) was stirred with 2 mole ratio of triethylamine in DMSO overnight. The ADR base (10 mg) with blended block copolymers (50 mg) at different weight ratios (100/0, 95/5, 90/10, 75/25, 60/40, and 0/100 wt % of polyHis/PEG to PLLA/PEG) were dissolved in 20 mL DMSO, transferred to a preswollen dialysis membrane (Spectra/Por molecular weight cut off 15,000) and dialyzed against HCl—$Na_2B_4O_7$ buffer solution (pH 9.0) for 24 hours at 4° C. The medium was exchanged several times and the content inside the dialysis tube was subsequently lyophilized. The amount of entrapped ADR was determined by measuring the UV absorbance at 481 nm of the drug-loaded polymeric micelles dissolved in DMSO.

Figure 12:
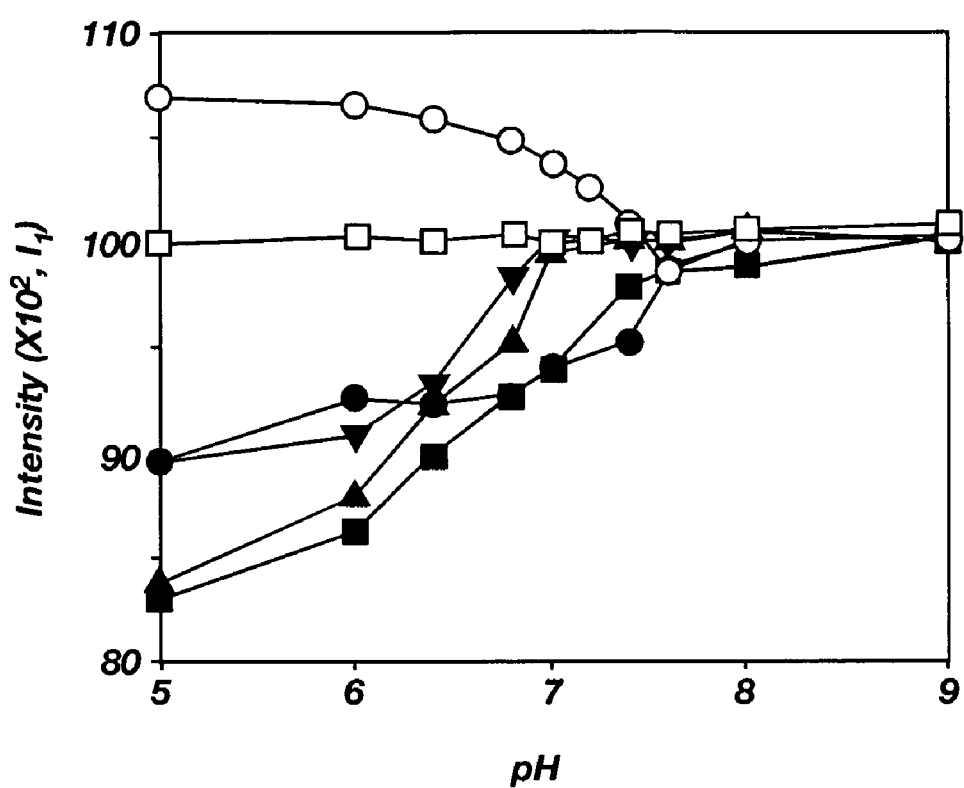
FIG. 12 shows pH-dependent relative turbidity ($T/T_i$%) of mixed micelles comprising polyHis/PEG and PLLA/PEG (PLLA/PEG content: 0 wt % (○); 5 wt % (●); 10 wt % (■); 25 wt % (▲); 40 wt % (▼); and 100 wt % (□)). Ti is the transmittance at 500 nm at pH 9.0, and T is the transmittance at a selected pH after micelles were stabilized for 24 h.

FIG. 12 shows the pH-dependent stability of the mixed micelles monitored by relative light transmittance ($T/T_i$%; the transmittance of the mixed micelle at each pH/transmittance at pH 9.0). The $T/T_i$% of polyHis/PEG micelle slightly increased with decreasing pH, especially below pH 7.6, which is attributed to micelle destabilization followed by dissociation. PLLA/PEG micelle, being devoid of pH dependency, showed no change in turbidity and preserved its stability in the entire pH range tested. It is, however, interesting to note that the $T/T_i$% of the mixed micelles rather decreased with decreasing pH. This observation seems to be associated with ionization of polyHis/PEG, accompanied by separation and isolation of PLLA/PEG from the micelles, which in turn became segregated in water. This observation indirectly reflects the disintegration of the micelles by ionization of imidazole group along polyHis chains. The destabilizing pH was influenced by the amount of PLLA/PEG block copolymer in the mixed micelles. The addition of up to 10 wt % of PLLA/PEG to the micelle showed a slight shift in destabilizing pH. However, 25 wt % additions considerably enhanced the micelle stability at pH 7.4 and the destabilization occurred below pH 7.0. At 40 wt % PLLA/PEG blend, the destabilization pH was shifted a bit further downward with less release of PLLA/PEG albeit of its high content.

EXAMPLE 14 pH-dependent Adriamycin Release and Cytotoxicity

The pH-dependent micelle property prompted testing of the micelles for pH-induced drug release. When adriamycin was incorporated into the mixed micelles (0, 10, 25 and 40 wt % PLLA/PEG) during diafiltration, the micelle sizes ranged from 50 to 80 nm as determined by dynamic light scattering, as performed according to the procedure set out above. The drug loading efficacy was about 75-85% and the drug content in the micelles was 15-17 wt %.

The ADR loaded polymeric micelles were dispersed in 1 mL of phosphate buffer saline at different pHs. The solutions were transferred in a dialysis membrane tube (Spectra/Por MWCO 5,000), and the membrane was immersed in a vial containing 10 mL phosphate buffer saline solution at different pHs. The release of ADR from micelles was tested under the mechanical shaking (100 rpm) at 37° C. The outer phase of dialysis membrane was withdrawn and replaced with fresh buffer solution at predetermined time intervals to maintain sink conditions. The measurement of ADR concentration by a UV/VIS spectrophotometer was performed after adjusting each solution pH to 8.0 using 0.1 N NaOH solution.

Figure 13A:
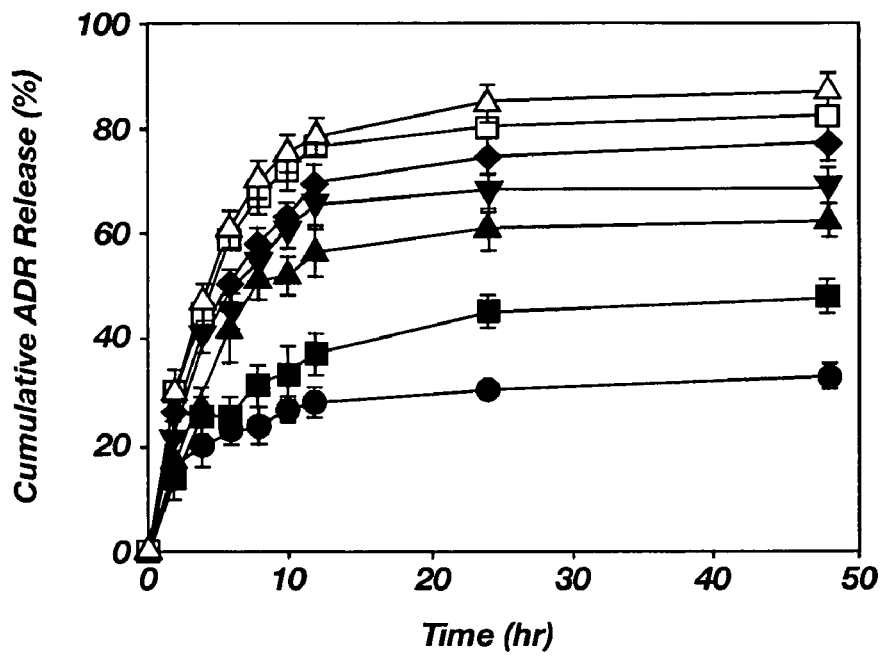
FIGS. 13A-B show pH-dependent cumulative ADR release from the mixed micelles comprising polyHis/PEG and PLLA/PEG (PLLA/PEG content in the mixed micelles.
Figure 13B:
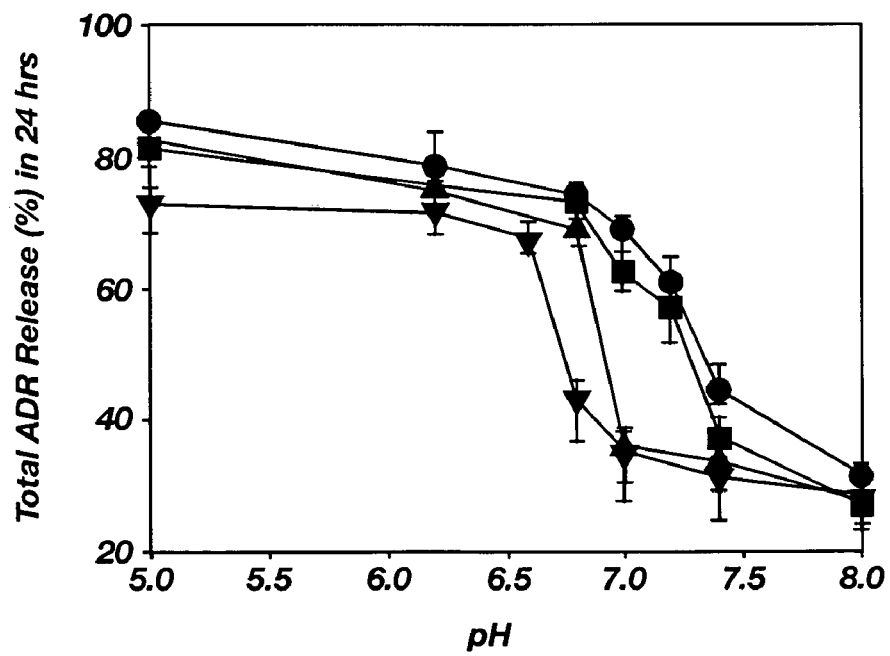

FIG. 13A shows the cumulative ADR release from polyHis/PEG micelles. The ADR release pattern followed nearly first-order kinetics and reached a plateau in 24 hours and 30 wt % of loaded ADR was released for 24 hours at pH 8.0. The release rate was accelerated by decreasing pH. The pH-dependent release patterns of the mixed micelles are presented in FIG. 13B by plotting cumulative amount of ADR for 24 hours vs. release medium pH. The mixed micelles containing 25 wt % PLLA/PEG showed a desirable pH-dependency such that 32 wt % of ADR was released at pH 7.0 and 70 wt % of ADR at pH 6.8 and 82 wt % at pH 5.0. On the other hand, the mixed micelles containing 40 wt % of PLLA/PEG suppressed the release of ADR to 35 wt % at pH 6.8 but 64 wt % at pH 6.6. This indicates that the content of PLLA/PEG controlled pH-dependent release from the mixed micelles by destabilization and the transition pH coincided with the results shown in FIG. 12. These results support the idea that the mixed micelles truly recognize the minute difference in pH and discriminate the tumor pH by destabilization and release rate.

Human breast adenocarcinoma (MCF-7) cells were obtained from Korean Cell Line Bank (KCLB). They were maintained in RPMI-1640 medium with 2 mM L-glutamine, 5% penicillin-streptomycin, 10% fetal bovine serum in a humidified incubator at 37° C. and 5% $CO_2$ atmosphere.

The cells ($5 \times 10^4$ cells/mL) growing as a monolayer were harvested by 0.25% (w/v) trypsin-0.03% (w/v) EDTA solution. The cells in 200 mL of RPMI 1640 medium were seeded in a 96-well plate for 24 hours before test. Free ADR or ADR-loaded micelle in HCl-$Na_2B_4O_7$ buffer solution (ADR 5 mg/mL, pH 9.0) was filtered through 0.2 mm syringe filters to make a stock solution. After measuring ADR concentration, the solution was diluted to make ADR or the micelle solutions with various ADR concentrations (100× the final concentrations (1, 10, 100, 1000, 5000 and 10000 ng/mL)) used for cell cytotoxicity tests. Each solution (10 µL) was diluted again with 990 µL of RPMI 1640 cell culture medium prepared from phosphate buffered saline solution. The pH of the culture medium containing free ADR or ADR loaded micelle was adjusted with 0.1 N HCl, or 0.1 N NaOH at a desired pH in the pH range of 6.6-8.0 prior to use. No significant pH drift in the culture medium was observed especially when ADR concentrations above 100 ng/mL during 48 hours. When a minor pH change was observed after 24 hours, the culture medium was collected from the cell culture plate and its pH was adjusted with 0.01 N HCl or 0.01 N NaOH. After 48 hours incubation at varying pH and ADR concentration, the cells were washed three times with phosphate buffer saline (pH 7.4). For cytotoxicity tests of blank micelles against MCF-7 cells, blank micelle concentrations (0.01, 0.1, 1, 10, 50 and 100 µg/mL) with different pHs (pH 6.6-7.4) in RPMI 1640 medium were prepared as described above, in the absence of ADR. Chemosensitivity was assessed using the tetrazolium salt MTT assay to measure the viability of tumor cells. 100 µL of medium containing 20 µL of MTT solution was added to each well, and the plate was incubated for an additional 4 hours, and then 100 µL of dimethylsulfoxide (DMSO) was added to each well. The solution was vigorously mixed to dissolve the reacted dye. The absorbance of each well was read using a microplate reader using a test wavelength of 570 nm and a reference wavelength of 630 nm.

Figure 14:
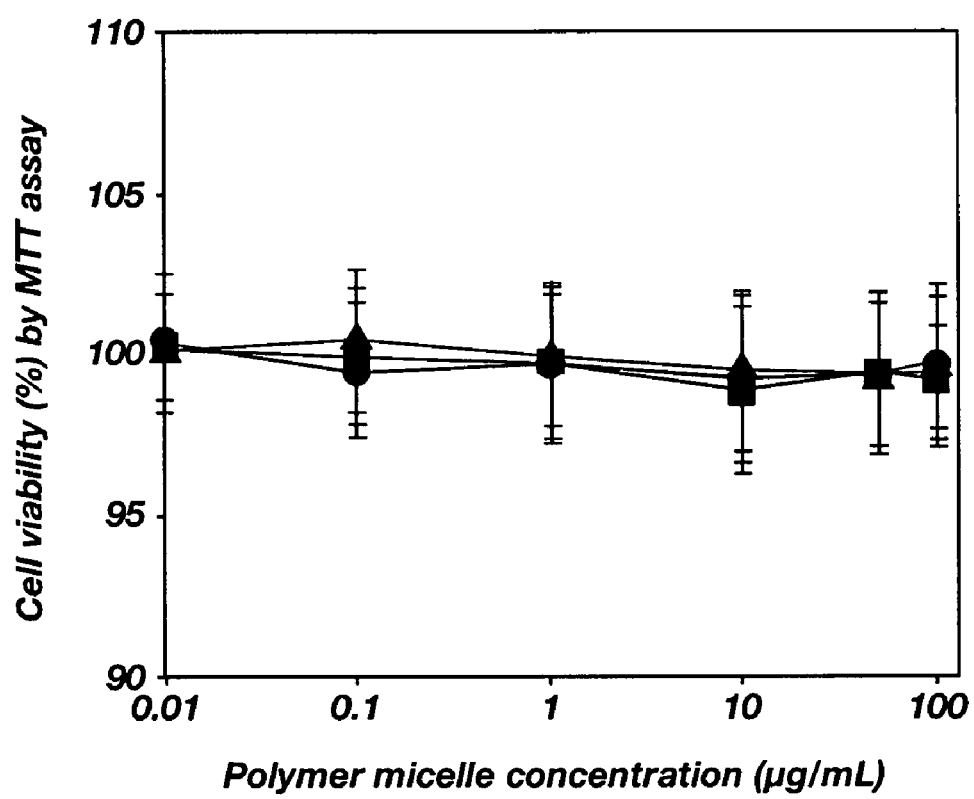
FIG. 14 shows the cytotoxicity of blank micelles against MCF-7 cells at pH 7.4 after 48 h incubation: PLLA/PEG micelles (●); polyHis/PEG micelles (■); and mixed polyHis/PEG and PLLA/PEG micelles with PLLA/PEG 25 wt % (▲).

When the blank micelles were tested with human breast adenocarcinoma (MCF-7) cells, no cytotoxicity was observed up to 100 µg/mL of polymeric micelle for 48 hours culture (FIG. 14) regardless of the culture medium pH. However, ADR-loaded micelles presented tumor cell killing activity in a pH-dependent manner.

Figure 15A:
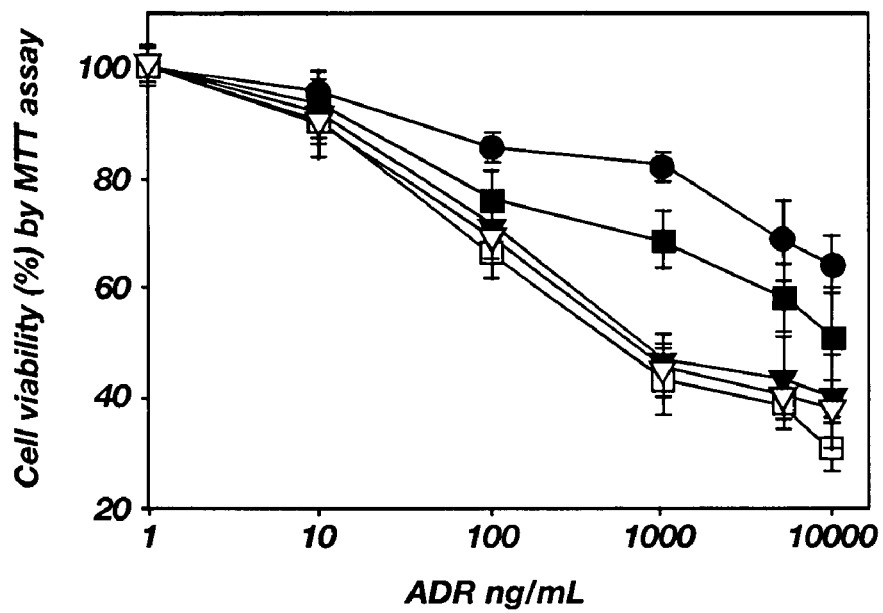
FIGS. 15A-E show the cytotoxicity of ADR-loaded mixed micelles with PLLA/PEG content of 0 wt % (FIG. 15A), 10 wt % (FIG. 15B), 25 wt % (FIG. 15C), 40 wt % (FIG. 15D), and 100 wt % (FIG. 15E) after 48 h incubation at varying pH: pH 7.4 (●); pH 7.2 (■); pH 7.0 (▲); pH 6.8 (▼); and pH 6.6 (♦). Free ADR toxicity is presented as a reference at pH 7.4 (○); pH 7.2 (□); pH 7.0 (△) ; pH 6.8 (▽); and pH 6.6 (◇).
Figure 15B:
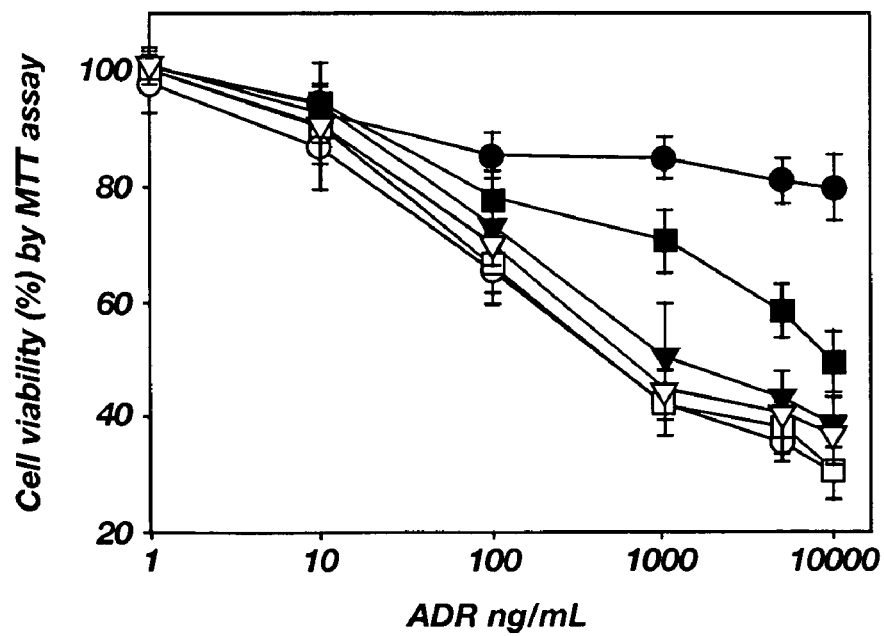
Figure 15C:
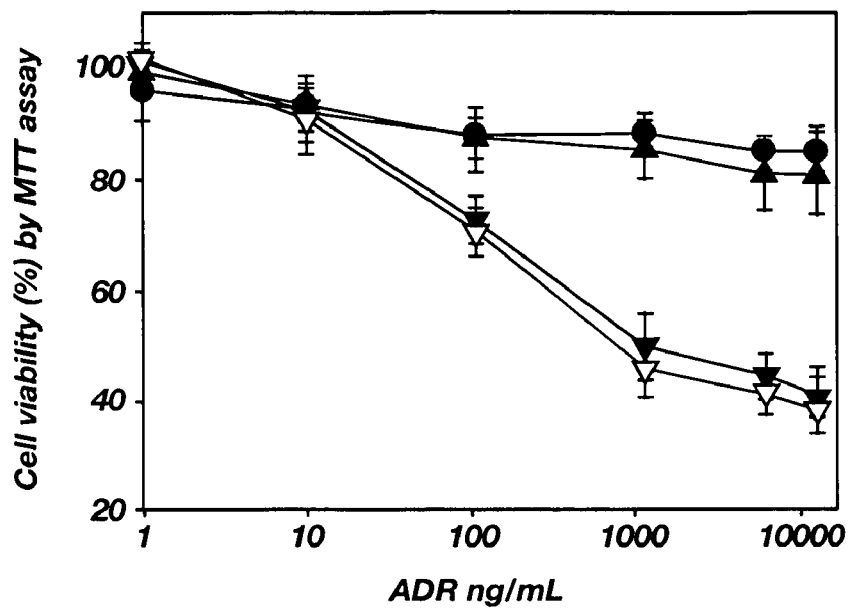
Figure 15D:
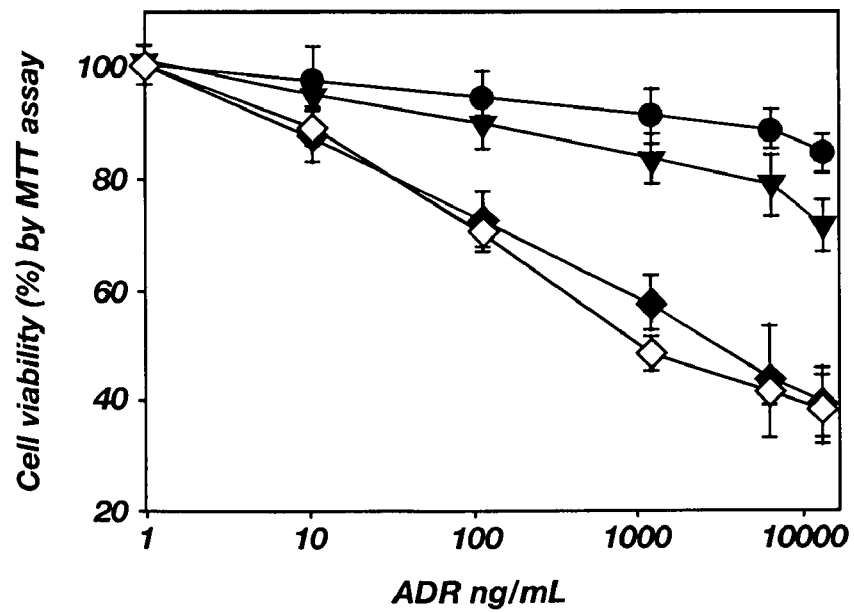
Figure 15E:
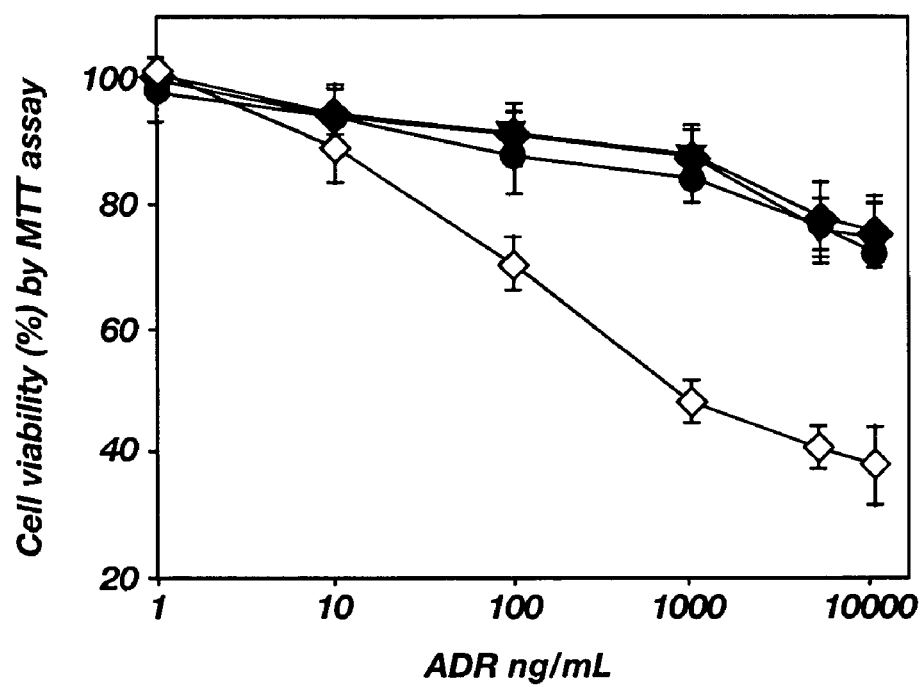

ADR loaded polyHis/PEG micelles demonstrated a certain degree of cell killing effect at pH 7.4 because of a certain degree of micelle instability and ADR release. But the cell viability was much reduced at pH 6.8 under the influence of enhanced ADR release (FIG. 15A). The mixed micelles with 10 wt % PLLA/PEG (FIG. 15B) caused less cytotoxicity at pH 7.4 and high cell killing effect below pH 7.2. The above results are distinguished from the cytotoxicity of free ADR which is almost independent of pH. The 25 wt % PLLA/PEG micelle (FIG. 15C) appeared more sensitive to pH, especially differentiating between pH 7.0 and 6.8. 40 wt % PLLA/PEG micelle (FIG. 15D) distinguished pH 6.8 and 6.6 in cytotoxicity. Considering that 100 wt % PLLA/PEG micelle (FIG. 15E) had no pH-dependent cytotoxicity and no cytotoxicity of blank micelles, the pH-dependent cytotoxicity solely relies on the release of ADR at different pH. The change in pH from 8.0 to 6.6 may influence cell surface charges and cellular physiology and viability, noting that the low pH is a favorable environment for tumor cells but opposite effect on normal cells. The cell viability expressed in this study is relative to those at different pH in the absence of ADR and the direct pH effect on the cell viability was not monitored with MCF-7 cell line. No noticeable difference in cell viability by pH with free ADR was observed.

EXAMPLE 15

Folate-Conjugated Mixed Micelles

Endogenous folic acid, a vitamin B essential for cell life, has been utilized for tumor targeting of anticancer drugs, radiopharmaceuticals, S. D. Weitmann et al., supra; J. F. Ross et al., supra; P. S. Low & R. J. Lee, supra; J. A. Reddy & P. S. Low, supra, and genes via folate receptor-mediated endocytosis. The receptors are highly expressed on various tumors such as ovarian, lung, breast, brain, colon, and kidney cancers. S. D. Weitmann et al., supra; J. F. Ross et al., supra. After being internalized, the carriers exist mainly in endosomes or multivesicular bodies (MVD) and less in lysosomes. J. A. Reddy & P. S. Low, supra. The pH-sensitive liposomes with anticipated fusogenic activity therefore have been utilized for drug release out of endosomes O. V. Gerasimov et al., supra; O. Meyer et al., Copolymers of N-isopropylacrylamide can trigger pH sensitivity to stable liposomes, 421 FEBS Lett. 61-64 (1998); P. S. Low & R. J. Lee, supra. Indeed, ADR entrapped in a pH-sensitive liposome-PEG that decorated with folate, enhanced cytotoxicity against tumor cells by a maximum of 86-fold compared to free ADR due to high uptake rate of the liposomes even for a short period of incubation time (2 hrs). P. S. Low & R. J. Lee, supra.

For active internalization of the micelles, folic acid was introduced into the pH-sensitive mixed micelle. After internalization, the micellar carrier actions can be combined with pH-triggered ADR release at early endosomal pH and the fusogenic activity of polyHis, which helps ADR release from endosomal compartment to cytosol. PolyHis has been reported for its fusogenic activity, J. M. Benns et al., supra; D. Putnam et al., supra; C. Y. Wang & L. Huang, supra, but the mechanism of its fusogenic activity remains unclear, and has been hypothesized with (i) the proton-sponge effect of polyHis due to protonation of imidazole at slightly acidic pH, J. M. Benns, supra, and (ii) charge-charge interaction, C. Y. Wang & L. Huang, supra, between endosomal membrane and poly(L-histidine).

Figure 16A:
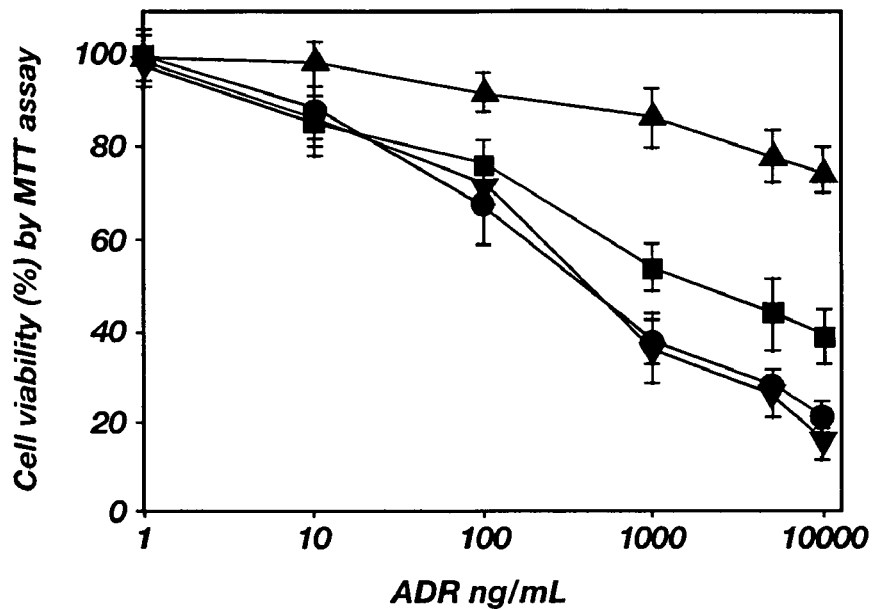
FIGS. 16A-B show the cytotoxicity of (FIG. 16A) free ADR (●), polyHis/PEG-folate micelles (■), PLLA/PEG-folate micelles (▲), and polyHis/PEG-folate and PLLA/PEG-folate mixed micelles (25 wt % PLLA/PEG-folate) (▼) at pH 8.0, and of (FIG. 16B) polyHis/PEG-folate and PLLA/PEG-folate mixed micelles comprising 25 wt % PLLA/PEG-folate (closed symbols) or 40 wt % PLLA/PEG-folate (open symbols) at pH 7.4 (●, ○) and pH 6.8 (■,□) against MCF-7 cells after 48 h incubation.
Figure 16B:
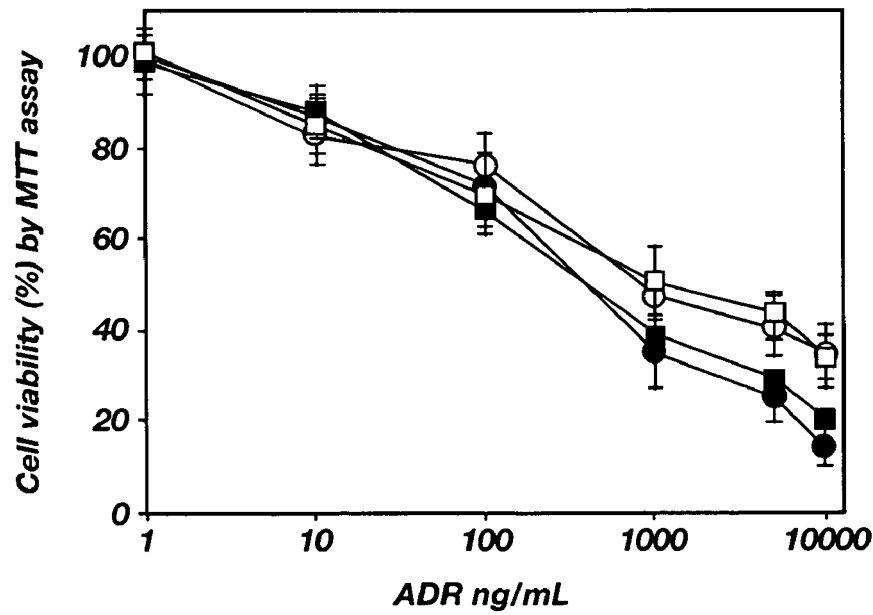

FIGS. 16A-B demonstrate such combined effects. The ADR loaded polyHis/PEG-folate micelles induced greatly enhanced cytotoxicity (cell viability 40% at ADR 10 µg/mL at pH 8.0 (this pH was employed to ensure the micelle stability before internalization)), while the PLLA/PEG-folate show a slight increase in cytotoxicity. This is well contrasted with that of without folate conjugation where was no noticeable difference in cytotoxicity (cell viability 80% at ADR 10 µg/mL) of these two micelles at pH 8.0. These observations clarify the role of polyHis in anticancer activity by destabilization for drug release and fusogenicity. Besides, it was found that the mixed micelle containing 25 wt % PLLA/PEG was more efficacious (cell viability 16% at ADR 10 µg/mL).

FIG. 16B indicates that, once internalization by folate receptors grew predominant, the pH effect on drug release became insignificant. This observation can be explained by the fact that (i) the mixed micelles were internalized into tumor cells via folate-receptor mediated endocytosis and underwent destabilization in slightly acidic early endosomal compartments by protonation of imidazole group and (ii) ADR released from the mixed micelles under influence of extracellular pH, regardless of folate-receptor mediated endocytosis, is also effective drug portion for cell killing (FIGS. 15A-E). It is thought that because the extracellular pH in a solid tumor is heterogeneous with a distribution as a function of distance from capillary, G. R. Martin & R. K. Jain, Noninvasive measurement of interstitial pH profiles in normal and neoplastic tissue using fluorescence ratio imaging microscopy, 54 Cancer Res. 5670-5674 (1994), the mixed mechanisms of triggered release in the extracellular space and/or for cytosolic delivery after internalization in the in vivo situation may occur. This is expected to be beneficial to treat solid tumors by minimizing the "road block" effect of the particles after extravasation due to the micelle destabilization and internalization into the tumor cells, increasing local concentration for drug diffusion to remote tumor cells as well as passive diffusional internalization in conjunction with more active internalization.

The effect of PLLA/PEG in the ADR-loaded mixed micelle against MCF-7 cells was apparent in FIG. 16B, although its mechanism was not clear, as compared to the cytotoxicity of polyHis/PEG micelles tested at pH 8.0 to endow the micelle stability before internalization. The 25 wt % PLLA/PEG-folate in ADR-loaded mixed micelles showed 16-20% cell viability by ADR released in or out of cells. The micelle with 40 wt % PLLA/PEG-folate was attributed to slightly decreased cytotoxicity (cell viability 34% at ADR 10 µg/mL) and this probably was due to decreased pH-sensitivity and slower release kinetics of ADR even at low pH.

Figure 17:
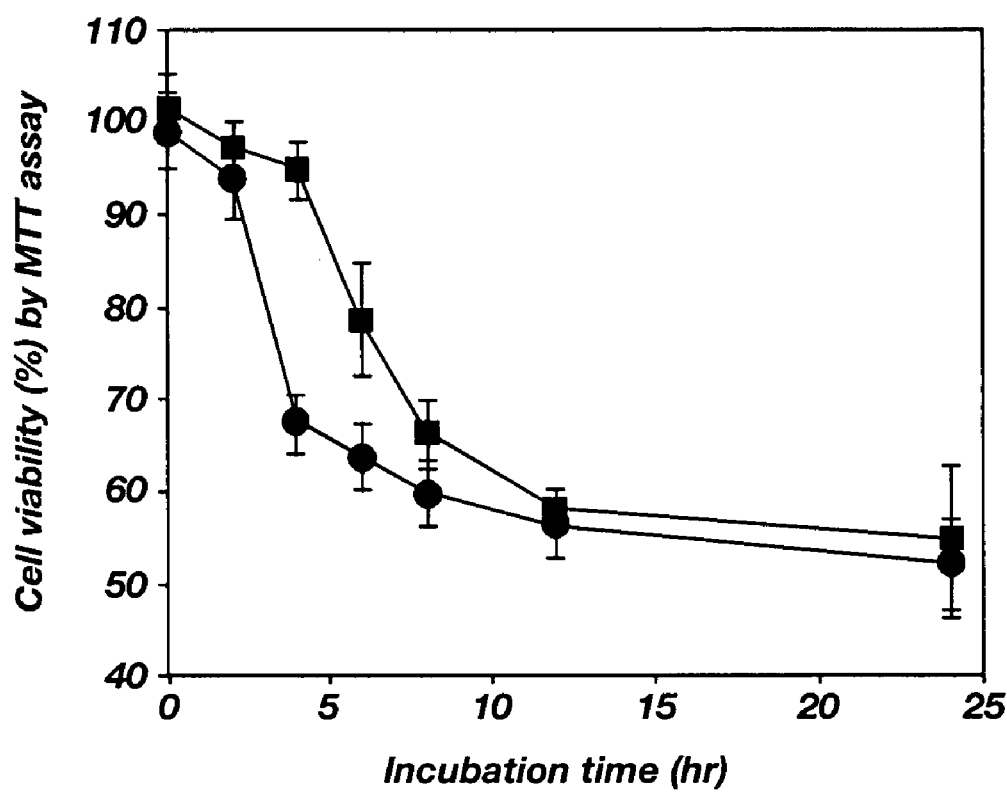
FIG. 17 shows the cell killing rate against MCF-7 cells treated with polyHis/PEG-folate and PLLA/PEG-folate mixed micelles (25 wt % of PLLA/PEG-folate) (●) and free ADR (■) at pH 6.8. The ADR content in the micelles was adjusted to be equivalent to the free ADR concentration (500 ng/ml) and MCF-7 cells were treated for a selected incubation time.

FIG. 17 shows the cell killing rates of the mixed micelles and free ADR. At pH 6.8, the ADR-loaded mixed micelle may exhibit two separated mechanisms of drug availability to the cells as mentioned before, i) the ADR release inside of cell after internalization and (ii) outside of cell via pH-responsive ADR release. However, free ADR diffuses only to cells passively. Unlike free ADR, therefore, folate-conjugated mixed micelles facilitated faster cell killing in 0-4 hrs incubation and confined to slow cell killing rate at 4-24 hrs. This observation is consistent with the high affinity of folate-receptors on tumor cells. In addition, there is little difference in cell killing rate between pH 6.8 and pH 7.4 (data not shown), thus explaining quick cytotoxic action of ADR-loaded mixed micelles against MCF-7 cells due to the active internalization. P. S. Low & R. J. Lee, supra; J. A. Reddy & P. S. Low, supra.

Figure 18A:
FIGS. 18A-C show confocal images of MCF-7 cells treated with (FIG. 18A) polyHis/PEG-folate and PLLA/PEG-folate mixed micelles (25 wt % of PLLA/PEG-folate), (FIG. 18B) PLLA/PEG-folate micelles, and (FIG. 18C) free ADR.
Figure 18B:
Figure 18C:

To visualize the effect of folate-mediated endocytosis and fusogenic activity of the mixed micelles, the distribution of ADR on MCF-7 cells was observed by confocal microscopy (FIGS. 18A-C). The intracellular distribution of ADR was observed with the cells grown on a Lab-Tek$^R$ II chamber slide (Nalge Nunc International, Naperville, Ill.). The RPMI 1640 medium (pH 6.8) containing free ADR or ADR-loaded micelle for cell culture was prepared as described above. The ADR concentration used was 1000 ng/mL in free ADR solution or micelle solutions. The treated cells with the micelles or free ADR were washed three times with phosphate buffer saline (pH 7.4) aqueous solution after 1 hr incubation. The cells were fixed with 1% formaldehyde in phosphate buffer saline for 10 min at room temperature. A coverslip was mounted on a glass microscope slide with a drop of anti-fade mounting media (5% n-propyl galate, 47.5% glycerol and 47.5% Tris-HCl, pH 8.4) to reduce fluorescence photo bleaching. ADR distribution was examined by confocal microscopy (Leica TCS NT, Leica, Germany) at excitation and emission wavelengths of 488 nm and 510 nm, respectively. By one hour incubation time, the folate-conjugated micelles were rapidly taken up by the cells. The folate-conjugated mixed micelle and PLLA/PEG-folate micelles showed high intracellular ADR concentration, which was visualized by red-intensity of ADR. Nevertheless, in the case of PLLA/PEG-folate micelles (FIG. 18B), ADR significantly localized probably in endosomes instead of broad distribution of ADR in cytosolic compartment. This observation is clearly distinguished from that of the folate-conjugated mixed micelle with fusogenic activity. ADR carried by the mixed micelles strikingly promoted cytosolic distribution of ADR (FIG. 18C). In contrast, for free ADR (FIG. 18A), only low red-intensity appeared in the peripheral region of the cells due to slow diffusion process into the cells for one hour incubation period.

PolyHis/PEG (or polyHis/PEG-folate) was constituted to novel pH-sensitive polymeric mixed micelles with PLLA/PEG (or PLLA/PEG-folate). This blending shifted ADR triggering pH from 7.4 to 7.2-6.6. In in vitro the cell viability study, it was found that the ADR-loaded mixed micelles were advantageous for tumor cell killing because the triggering pH for ADR release was around tumor $pH_e$ (pH 7.2-6.6) and there was minimal cytotoxicity at pH 7.4. Furthermore, the introduction of folate into mixed micelles enhanced the cell killing effect by active internalization. The fusogenic activity of polyHis in endosomes facilitated cytosolic delivery of ADR and explained the improved cytotoxicity of the micelles to tumor cells. The combined mechanisms of pH-triggered release and active internalization can be beneficial to treat solid tumors by minimizing the "road block" effect of the particles after extravasation, increasing local concentration for drug diffusion and more active internalization, but this hypothesis requires further investigation for proof.

Adriamycin Release from Endosomal Compartments

A major limitation of chemotherapy is the multidrug resistance (mdr) phenotype of tumor cells. Although numerous studies on the reversal of mdr have been done, M. M. Gottesman & I. Pastan, 62 Ann. Rev. Biochem. 385-427 (1993); F. Thiebaut et al., 84 Proc. Nat'l Acad. Sci. USA 7735-7738 (1987); N. Baldini et al., 68 Eur. J. Cell Biol. 226-239 (1995); M. M. Gottesman et al., 6 Curr. Opin. Genet. Dev. 610-617 (1996); S. Dey et al., 97 Proc. Nat'l Acad. Sci. USA 10594-10599 (1997, the treatment of mdr still remains unsolved.

One of the major mdr factors, P-glycoprotein (pgp), which is encoded in humans by the MDR1 gene and is a member of the evolutionary highly conserved family of the ATP-binding cassette transporters, F. Thiebaut et al., supra; N. Baldini et al., supra, is over-expressed on the plasma membrane of various tumor cells, which plays an important role by pumping antitumor drug out of tumor cells. As an energy-dependent drug-efflux pump, it lowers intercellular drug concentration below cytotoxic threshold by extruding antitumor drug from the cells. M. Kool et al., 57 Cancer Res. 3537-3547 (1997); S. P. C. Cole et al., 258 Science 1650-1654 (1992).

Therefore, N-(2-hydroxypropyl)methacrylamide (HPMA) copolymer bound doxorubicin (DOX), J. Kopecek et al., 50 Eur. J. Pharm. Biopharm. 61-81 (2000), polyalkylcyanoacrylate nanoparticles, C. E. Soma et al., 21 Biomaterials 1-7 (2000), liposomal drug formulations, Y. L. Lo et al., 21 Anticancer Res. 445-450 (2001), and others have been suggested and developed for overcoming P-glycoprotein.

Recently, the doxorubicin-PLURONIC® block copolymers formulation (SP1049C), A. V. Kabanov et al., 82 J. Contr. Release 189-212 (2002), showed inhibition of tumor growth 3.46-times greater than free doxorubicin against BDF1 mice bearing resistant P388/DOX cells and 7.46 times greater against BALB/c nude mice bearing resistant MCF-7/DOX$^R$ cells. It was reported that the PLURONIC® block copolymers generally inhibit P-glycoprotein activity through an ATP-depletion mechanism, A. V. Kabanov et al., supra, and result in the higher energy consumption in mdr cells.

Furthermore, it was hypothesized that a folate-PEG-liposomal carrier may bypass P-glycoprotein through nonlysosomal route like folate receptor-mediated endocytosis, D. Goren et al., 6 Clinical Cancer Res. 1949-1957 (2000), albeit relatively poor results were obtained in in vitro cell experiments due to the stability of the liposomes at pH 5.0-6.0 and limited fusogenic activity.

Considering the activity of polymers in intracellular compartments and the specificity of targeting, the pH-sensitive mixed micelles described herein were examined for the likelihood that the targeted micelles are taken up by tumor cells with overexpressed folate receptor (FR), J. A. Reddy & P. S. Low, 15 Crit. Rev. Ther. Drug Carrier Syst. 587-627 (1998); C. Pichon et al., 53 Adv. Drug Deliv. Rev. 75-94 (2001), and disrupted simultaneously under endosomal pH influence, thus finally presenting drug release from endocytosed micelles. The known fusogenic activity and amphoteric property of polyHis, J. M. Benns et al., supra; D. Putnam et al., supra; A. Patchornik et al., supra, support cytosolic drug delivery. Consequently, it was investigated whether polyHis-based mixed micelles avoid or overcome P-glycoprotein.

EXAMPLE 16

Figure 19A:
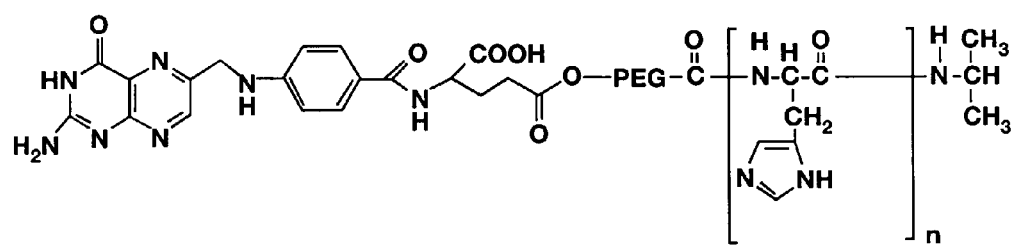
FIGS. 19A-B show the structures of polyHis/PEG-folate (FIG. 19A) and PPLA/PEG-folate (FIG. 19B).
Figure 19B:
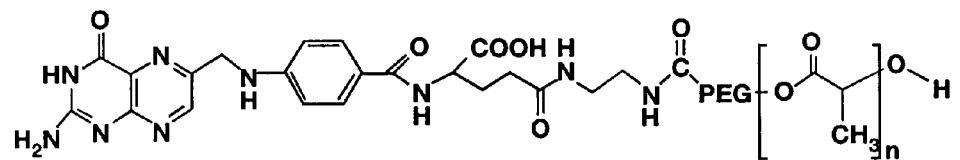

Poly(L-histidine) (polyHis, MW 5K)/PEG(MW 2K)-folate (FIG. 19A) and PLLA (MW 3K)/PEG (MW 2K)-folate (FIG. 19B) block copolymer were prepared for constructing pH-sensitive mixed micelles as described above. Before loading doxorubicin to the mixed micelle, doxorubicin-HCl (DOX-HCl, Sigma Chemical) was stirred with 2 mole ratio of triethylamine (Sigma Chemical) in DMSO (J.T. Baker) overnight. The DOX base (10 mg) with blended block copolymers (50 mg, 75/25 wt % of polyHis/PEG-folate to PLLA/PEG-folate) or PLLA/PEG-folate (50 mg) or polyHis/PEG-folate copolymer (50 mg) were dissolved in 20 mL DMSO and transferred to a pre-swollen dialysis membrane (Spectra/Por molecular weight cut off 15,000) and then dialyzed against NaOH—$Na_2B_4O_7$ (Sigma Chemical) buffer solution (pH 9.0) for 24 hours at 4° C. The medium was exchanged several times and the contents inside the dialysis tube were subsequently lyophilized. The amount of entrapped DOX was determined by measuring the UV absorbance at 481 nm of the drug loaded polymeric micelles dissolved in DMSO. The drug loading efficacy was about 75-85 wt % and consequently the DOX amount in micelles based on pH-sensitive micelles (PHSM) was 0.15-0.17/1.0 (DOX/polymer) ratio.

DOX-resistant MCF-7 cells (MCF-7/$DOX^R$) were selected from MCF-7 cells (Korean Cell Line Bank (KCLB)) that were stepwise exposed at 0.001-10 mg/mL of free DOX. Here, cells were maintained in RPMI-1640 (Gibco, Uxbridge, UK) medium with 2 mM L-glutamine, 5% penicillin-streptomycin, and 10% fetal bovine serum in a humidified incubator 37° C. and 5% $CO_2$ atmosphere.

To test whether or not P-glycoprotein was involved in the DOX resistant phenotype MCF-7 (MCF-7/$DOX^R$) subline, the resistant MCF-7/$DOX^R$ or wild MCF-7 cells ($1 \times 10^6$ cells) suspended in 200 mL phosphate buffer solution (PBS pH 7.4) containing 0.1% $NaN_3$ and 1% bovine serum albumin (Sigma) were incubated for 30 min at 4° C. with MRK-16 (Kamiya, Seattle, Wash.). After washing cells with ice-cold phosphate buffer solution containing 0.1% $NaN_3$ (Sigma), 1% bovine serum albumin, and 0.002% EDTA (Sigma), cells were centrifuged to remove unbound antibody and re-suspended in fresh PBS containing 0.1% $NaN_3$ and 1% bovine serum albumin. The cells were again incubated for 30 min at 4° C. with goat anti-mouse IgG fluorescein-conjugate (Sigma) used at a working dilution of 1:50. After washing, the cells were immediately analyzed on a flow cytometer (Becton Dickinson FacScan). As negative controls, MCF-7 or MCF-7/$DOX^R$ cells were incubated with only secondary antibody (goat anti-mouse IgG fluorescein-conjugate) for 30 min at 4° C. The fluorescence signal of cells treated only with secondary antibody were compared. A. Molinari et al., 59 Int. J. Cancer 789-795 (1994). For the cytotoxicity test of free DOX or drug-loaded polymeric micelles against sensitive MCF-7 or MCF-7/$DOX^R$ cells, cells ($5 \times 10^4$ cells/mL) growing as a monolayer, were seeded at 96-well dish in 200 mL of RPMI 1640 medium before 24 hrs. Free DOX or DOX loaded micelles in RPMI 1640 medium with pH 7.4 or 6.8 were prepared immediately before use as described above, added to medium-removed 96-well dish with different DOX concentration, and incubated for 48 hrs. Chemosensitivity was assessed using the tetrazolium salt MTT (Sigma Chemical Co.). Then, 100 mL of PBS pH 7.4 containing 20 mL of MTT (500 mg/L) solution was added to each well. The plates were incubated for an additional 4 hrs, and then 100 mL of DMSO was added to each well. The absorbance of each well was read on a microplate reader using a test wavelength of 570 nm and a reference wavelength 630 nm.

The analysis of intracellular distribution of DOX was carried out on MCF-7 or MCF-7/$DOX^R$ cells grown on a Lab-Tek$^R$ II chamber slide (Nalge Nunc International, Naperville, Ill.). The DOX content in micelles was adjusted to be equivalent to free DOX (1 mg/mL). The drug-treated cells at pH 7.4 for 1 hr incubation were washed three times with PBS pH 7.4 and then cells were fixed with 1% formaldehyde (J.T. Baker) in PBS for 10 min. A coverslip was mounted on a glass microscope slide with a drop of anti-fade mounting media (5% n-propyl galate, 47.5% glycerol and 47.5% Tris-HCl pH 8.4, Gibco Co., Uxbridge, UK). All specimens for the detection of DOX were examined under a confocal microscopy (Leica TCS NT, Leica, Germany) and the excitation and emission wavelengths were 488 nm and 510 nm, respectively.

Figure 20A:
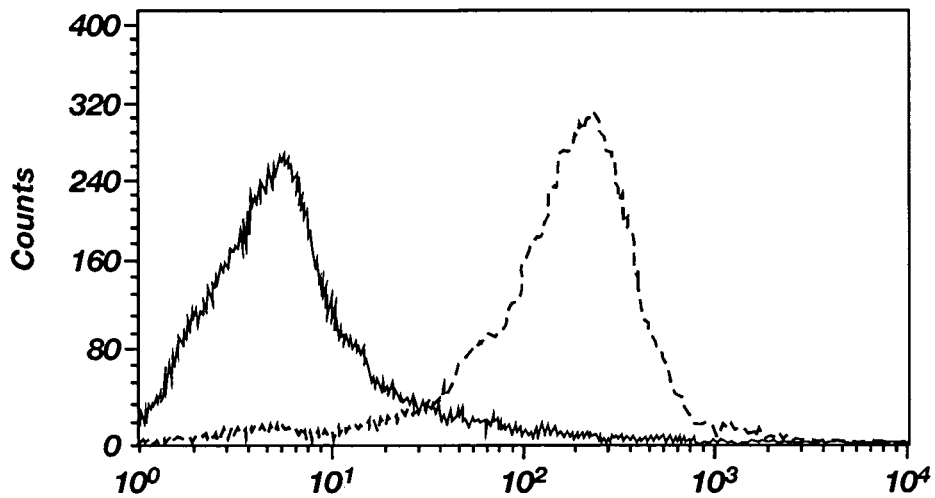
FIGS. 20A-B show characterization of multidrug resistance in MCF-7/DOX$^R$ cells.
Figure 20B:
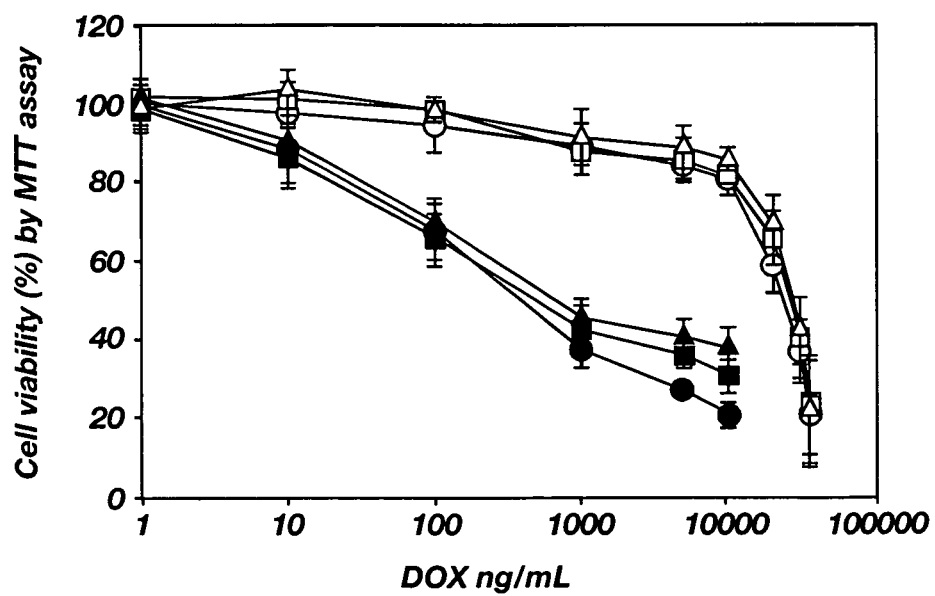

FIG. 20A shows the flow cytometric determination of P-glycoprotein on MCF-7/$DOX^R$ cells. The MRK-16 antibody specifically recognizes and binds to P-glycoprotein. A. Molinari et al., supra. The MRK-16 binding to P-glycoprotein was significantly detected in the MCF-7/$DOX^R$ cells. The MCF-7/$DOX^R$ showed a median fluorescence peak at approximately 218.5 compared to 6.23 for the sensitive MCF-7 cells. Here, the difference of fluorescence signal between MCF-7 and MCF-7/$DOX^R$ cells treated with only secondary antibody only was negligible. This result means that MCF-7/$DOX^R$ cells over-expressed P-glycoprotein by chronic exposure to DOX. In addition, FIG. 20B indicates the decreased cytotoxic action of free DOX against MCF-7/$DOX^R$ cells due to the over-expression of P-glycoprotein.

Figure 21A:
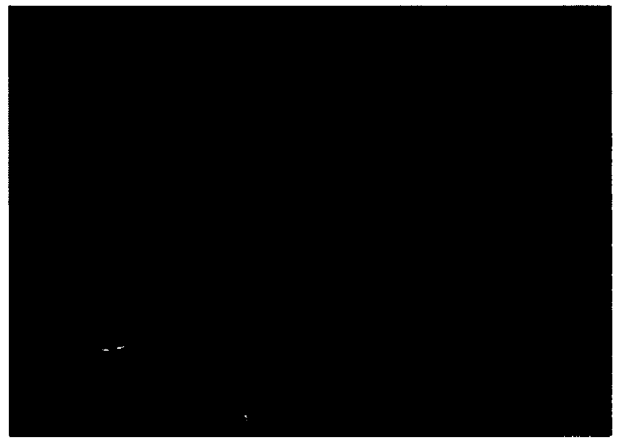
FIGS. 21A-B show confocal microscopy studies on (FIG. 21A) Dox-sensitive MCF-7, and (FIG. 21B) DOX-resistant MCF-7 (MCF-7/DOX$^R$) cells treated with free DOX at pH 6.8
Figure 21B:
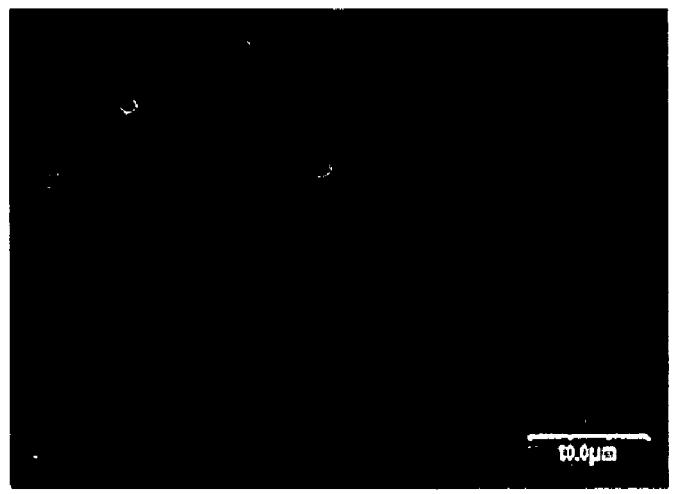

FIGS. 21A-B revealed a different distribution of DOX in MCF-7 cells (FIG. 21A) or MCF-7/$DOX^R$ (FIG. 21B). There was little DOX in cytosolic compartment resulting from response of P-glycoprotein, DOX-efflux pump, as shown in FIG. 21B. Unlike MCF-7/$DOX^R$ cells, DOX-sensitive MCF-7 cells accumulated much DOX in cytosolic compartment by passive diffusion of DOX (FIG. 21A). This visual observation suggests the effective DOX-efflux pump which blocks internalization of DOX and secretes DOX outside of cells.

Figure 22A:
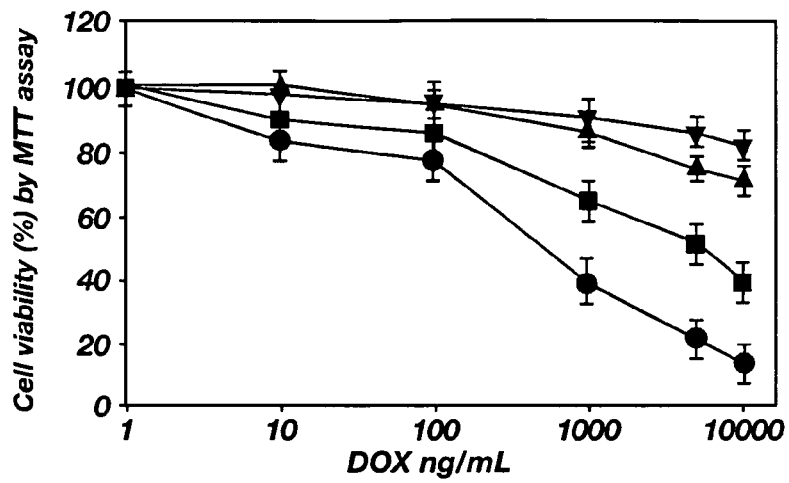
FIGS. 22A-C show the cytotoxicity of DOX loaded with pH-sensitive micelles (●), polyHis/PEG-folate micelles (■), PPLA/PEG-folate micelles (▲), free DOX (▼) against MCF-7/DOX$^R$ cells at (FIG. 22A) pH 8.0, (FIG. 22B) pH 7.4, and (FIG. 22C) pH 6.8 after 48 hrs incubation (n=7).
Figure 22B:
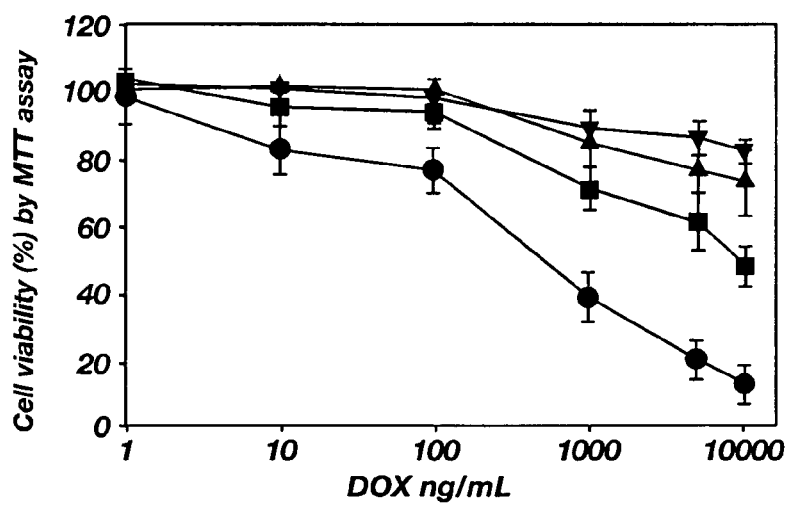
Figure 22C:
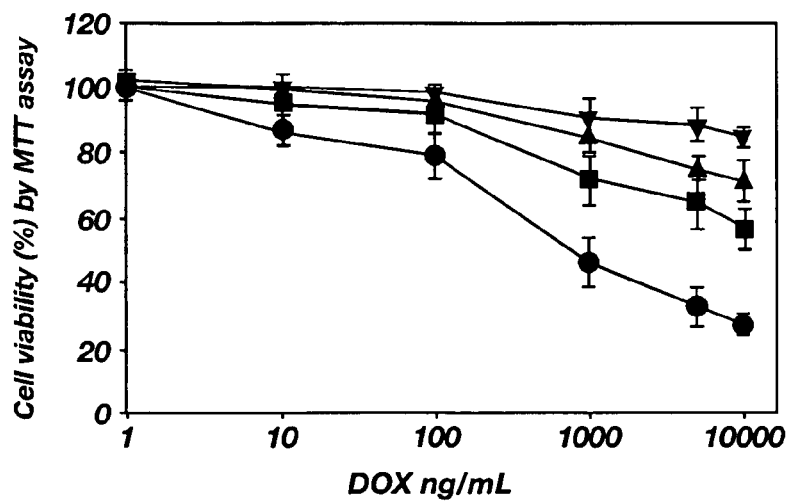

FIGS. 22A-C show the effect of free DOX or DOX-loaded micelles against MCF-7/$DOX^R$ cells. The viability of MCF-7/$DOX^R$ cells is little reduced at even high concentration of free DOX, which is corresponds to drug-efflux function of P-glycoprotein. Furthermore, even if it is hypothesized that folate receptor-mediated endocytosis route is not affected by P-glycoprotein, DOX-loaded PLLA/PEG-folate micelles do not show significant cytotoxicity against MCF-7/$DOX^R$ cells. This is much different from that DOX-loaded polyHis/PEG-folate micelles enhanced cytotoxicity. The proton-sponge effect of polyHis has been referred to as fusogenic activity because the charged polyHis reacts with the endosomal membrane. This fusogenic activity of polyHis exhibited a distinct difference as compared to PLLA/PEG-folate micelles, which is attributed to the avoiding of drug sequestration mechanism of mdr and the endosomal disruption by polyHis. In addition, FIG. 22A also indicates an interesting phenomenon in that the pH-sensitive micelles demonstrate improved cytotoxicity against MCF-7/$DOX^R$ cells than polyHis/PEG-folate micelle. There is presumably additional fusogenic activity, such as a certain reaction between PLLA/PEG-folate released from mixed micelle after destabilization in endosomal pH and endosomal membrane. This is consistent with results at pH 7.4 (FIG. 22B). The relevant mdr cell killing by PHSM is detected at pH 7.4, even if the cytotoxicity of DOX-loaded polyHis/PEG-folate micelles is reduced in studies because of relatively instability at pH 7.4.

FIG. 22C shows the feasibility of mdr reversal by pH-sensitive micelles at tumor extracellular pH, including that efficacy of mixed micelles at pH 6.8 was reduced a little bit because such micelles begins to be destabilized below pH 7.0 and DOX released outside the cells is not effective for killing MCF-7/DOX$^R$ cells. From this study, it is apparent that after folate receptor-mediated endocytosis, fusogenic activity of polymers released from disrupted micelles is responsible for mdr reversal of MCF-7/DOX$^R$ cells. Furthermore, folate receptor with higher affinity pH-sensitive micelles in an extent and contributes to mdr reversal of MCF-7/DOX$^R$ cells through endocytosis pathway even at pH 6.8. These cell viability results strongly support the feasibility that L-histidine based polymeric micelles can bypass the drug pumping mechanism of mdr cells via folate receptor mediated endocytosis.

Figure 23A:
FIGS. 23A-B show confocal microscopy studies on DOX-resistant MCF-7/DOX$^R$ cells treated with (FIG. 23A) DOX-loaded pH-sensitive micelles and (FIG. 23B) DOX-loaded PLLA/PEG-folate micelles at pH 6.8.
Figure 23B:

For further characterizing fusogenic activity of pH-sensitive micelles, confocal microscopy studies were done to verify distribution of DOX in cells. FIG. 23B shows the localized DOX distribution in MCF-7/DOX$^R$ cells treated with DOX-loaded PLLA/PEG-folate micelle at pH 6.8 in RPMI 1640 medium. The entrapped PLLA/PEG-folate micelles in endosome or multivesicular bodies (MVD) are responsible for the discrete punctuate DOX intensity and biased DOX intensity distribution. Such is conducted by the consequence of due to the absence of fusogenic activity. Unlike PLLA/PEG-folate micelle, pH-sensitive micelles (FIG. 23A) lead to, not only broad spreading of DOX in cytosolic compartments, but also increasing of DOX concentration inside of cells. As shown in FIGS. 22A-C, enhanced cytotoxicity of pH-sensitive micelles is again explained with (i) pH-dependent DOX release behavior and (ii) fusogenic activity of decomposed polymers from observing broader DOX intensity in cells.

Considering that the folate receptor is highly populated on solid tumor compared to normal cells, this drug delivery system will be effective for the specificity of tumor targeting for folate receptor-bearing solid tumors and treatment of tumor with mdr phenotype.

In Vivo Treatment of Warm-blooded Animals Using pH-Sensitive Mixed Polymeric Micelles for Drug Delivery

EXAMPLE 17

Growth Inhibition of Human Breast Carcinoma (MCF-7) Xenografts

A human breast carcinoma (MCF-7) cell line (ATCC, Manassas, Va.), which is known to over-express folate receptors on cell surfaces, was maintained in RPMI 1640 medium (Sigma Chemical Co., St. Louis, Mo.) with 2 mM L-glutamine, 1.5 g/L sodium bicarbonate, 1 mM sodium pyruvate, 0.01 mg/mL bovine insulin, 5% penicillin-streptomycin, and 10% fetal bovine serum in a humidified incubator at 37° C. and 5% CO2 atmosphere. Female nude mice (BALB/c mice, Charles River Laboratories, Wilmington, Mass.), 5-6 weeks old, were maintained in autoclaved microisolator cages housed in a positive pressure containment rack and cared under the guidelines of an approved protocol from University of Utah Institutional Animal Care and Use Committee.

To establish human breast cancer xenografts, a cell suspension (100 µL) containing 5×10$^6$ MCF-7 cells was injected into the left inguinal mammary line according to the procedure of P. J. Vickers et al., A multidrug-resistant MCF-7 human breast cancer cell line which exhibits cross-resistance to antiestrogens and hormone-independent tumor growth in vivo, 10 Mol. Endocrinol. 886-892 (1988). The MCF-7 cell line responds to estrogen with an increased level of progesterone receptors. However, the estrogen response is lost in MCF-7/DOX$^R$ cells. Therefore, MCF-7 tumor growth was facilitated by feeding 1 mg estrone (Sigma Chemical Co.) per 1 liter water to mice, according to the procedure of V. Dubois et al., CPI-0004Na, a new extracellularly tumor-activated prodrug of doxorubicin, 62 Cancer Res. 2327-2331 (2002). The administration of estrone in water to mice bearing MCF-7 xenografts was stopped one week before antitumor study.

Tumor volume was calculated using a formula, tumor volume=0.52×length×width×height. Dimensions were measured with an electronic digital caliper. Two to three weeks after inoculation (tumor volume 150-200 mm$^3$) in vivo antitumor studies were performed. Saline (control), free DOX, or DOX-loaded micelles in aqueous saline solution were injected intravenously through a tail vein by 1-3 bolus injections at three day intervals. The injection volume (approximately 0.1 mL/10 g body weight) of micelle preparation was adjusted to give 10 mg DOX/kg body weight. Five to eight mice per study were used. Tumor volume and body weight were monitored with elapsed time. A mean standard error was calculated for each experimental point.

For the preparation of doxorubicin-loaded micelles, doxorubicin.HCl (DOX-HCl, Sigma Chemical Co., St. Louis, Mo.) was desalted by stirring overnight in the presence of two molar equivalents of triethylamine (Sigma Chemical Co.) in DMSO (Sigma Chemical Co.). After DOX purification and drying, DOX (2 mg) and blended copolymers (20 mg) of polyHis-b-PEG-folate (or polyHis-b-PEG without folate) and pLLA-b-PEG-folate (or pLLA-b-PEG without folate) at a blending ratio of 75:25 by weight for pH-sensitive micelles (PHSM or PHSM/f, if conjugated with folate) or 0:100 for pH-insensitive micelles (PHIM or PHIM, if conjugated with folate), were dissolved in 10 mL DMSO. The mixture was transferred to a pre-swollen dialysis membrane (Spectra/Por molecular weight cut off 15,000) and then dialyzed against NaOH—Na$_2$B$_4$O$_7$ (Sigma Chemical Co.) buffer solution at pH 9.0. The buffer was replaced with fresh buffer at 1, 2, 4, 6, 12 and 24 h. The amount of entrapped DOX was determined by measuring UV absorbance at 481 nm of the drug after dissolving micelles in DMSO. The drug loading efficacy was about 75-85 wt % and, consequently, the amount of DOX in micelles based on the amount of blended polymer was 0.15-0.17/1.0 (DOX/polymer) weight ratio.

Figure 24A:
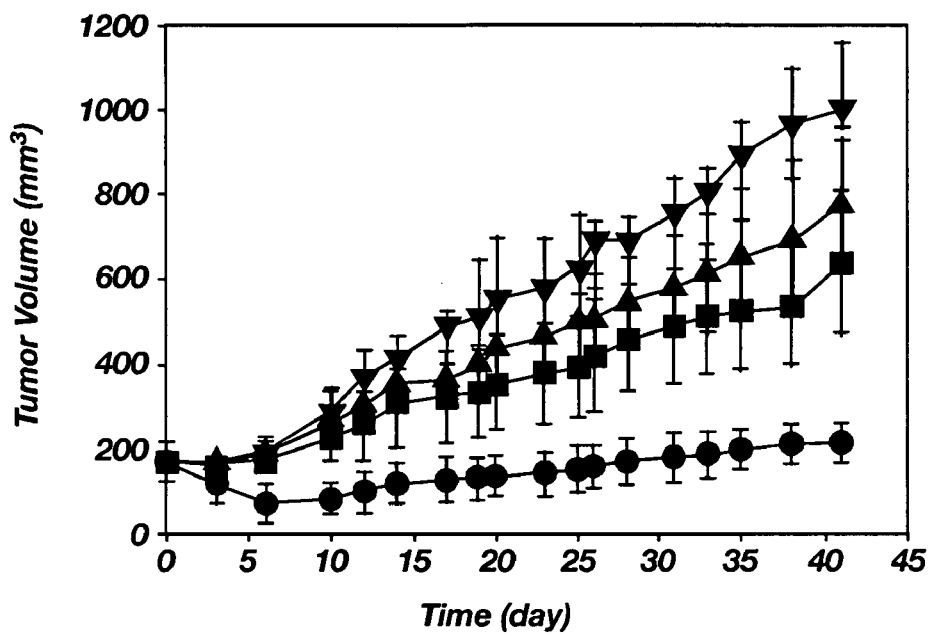
FIGS. 24A-B show in vivo tumor volume change (FIG. 24A) and body weight change (FIG. 24B) of human breast MCF-7 carcinoma xenografts in BALB/c nude mice injected intravenously with 10 mg/kg DOX equivalent dose: mixed micelles of polyHis-b-PEG and PLLA-b-PEG at a 75:25 weight ratio (●), PLLA-b-PEG micelles (■), free DOX (▲), and saline solution (▼); values are means±the standard deviation.
Figure 24B:
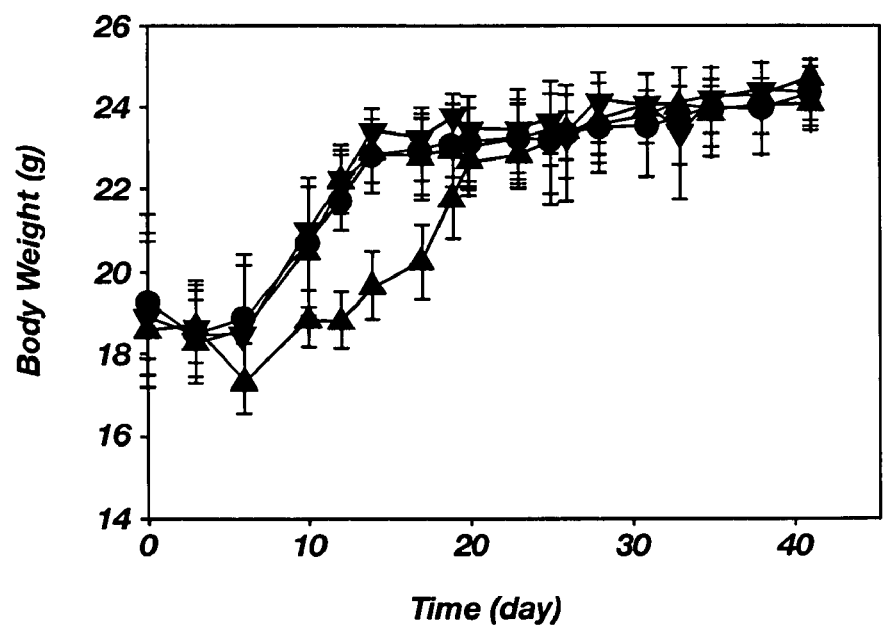

FIG. 24A shows the in vivo results of the anticancer activity of the tested DOX formulations injected intravenously on days 0 and 3. The DOX-loaded PHSM (equivalent DOX=10 mg/kg) exhibited significant inhibition (P<0.05 compared with free DOX or saline solution) of the growth of MCF-7 xenografts. The tumor volume of mice treated with the PHSM (P<0.05 compared with free DOX) was approximately 4.5 or 3.6 times smaller than that compared to saline solution or free DOX treatment after 6 weeks. The triggered release of DOX by tumor extracellular pH (pH$_e$<7.0) after accumulation of the micelle in the tumor sites via the enhanced permeation and retention (EPR) mechanism may present a more effective modality in tumor chemotherapy, providing higher local concentrations of the drug at tumor sites (targeted high-dose cancer therapy), while providing a minimal release of the drug in micelles during circulating in the blood (pH 7.4). When compared with PHIM, the volume of tumors treated with the PHSM was approximately 3.0 times smaller than that treated with PHIM (particle size=50-70 nm, data now shown) of which properties are not influenced by pH. In addition, the destabilization of PHSM (converting to unimers) may help extravasation of additional micelles from the blood compartment and their penetration into tumors by reducing the physical barrier effect, which can be generated by stable particles, such as conventional liposomes and polymeric micelles. It was reported that drug carriers, such as PEG modified liposomes, are in an insoluble form and only reside in the vicinity of the leaky blood vessels after extravasation, rather migrating into the deep sites of tumors. This "road block effect" could obstruct the additional accumulation of the carriers at tumor sites. It is interesting to note that only PHSM administration showed decreased tumor size for initial one week. No obvious changes in mice body weight in experimental groups except free DOX were observed. Free DOX caused more weight loss after intravenous administration (FIG. 24B) than micelle formulations.

EXAMPLE 18

Growth Inhibition of Human Breast Carcinoma (MCF-7/DOX$^R$) Xenografts

Figure 25A:
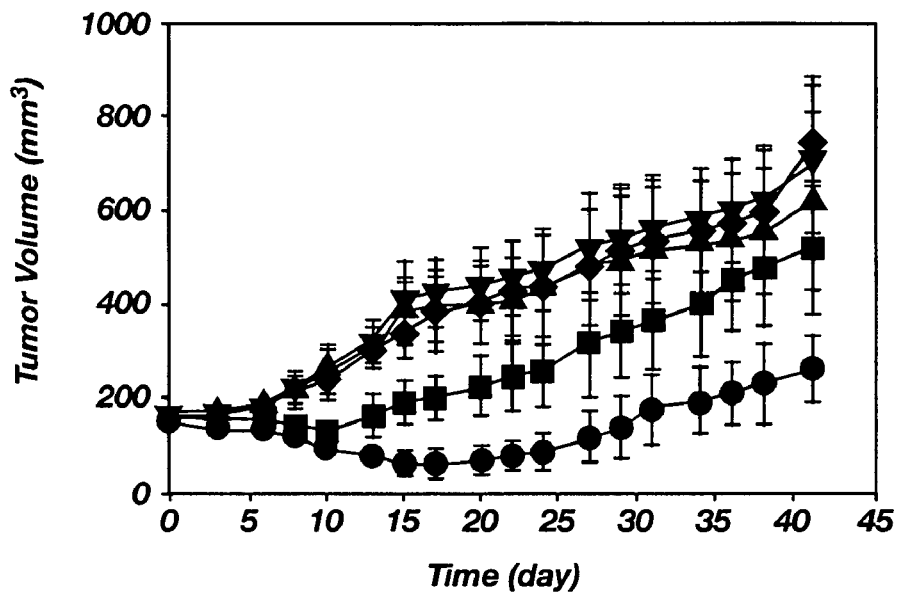
FIGS. 25A-B show in vivo tumor volume change (FIG. 25A) and body weight change (FIG. 25B) of human breast MCF-7/DOX$^R$ carcinoma xenografts in BALB/c nude mice injected intravenously with 10 mg/kg DOX equivalent dose: mixed micelles of polyHis-b-PEG-folate and PLLA-b-PEG-folate at a 75:25 weight ratio (●), mixed micelles of polyHis-b-PEG and PLLA-b-PEG at a 75:25 weight ratio (■), PLLA-b-PEG-folate micelles (▲), PLLA-b-PEG micelles (▼), and free DOX (♦); values are means±the standard deviation.
Figure 25B:
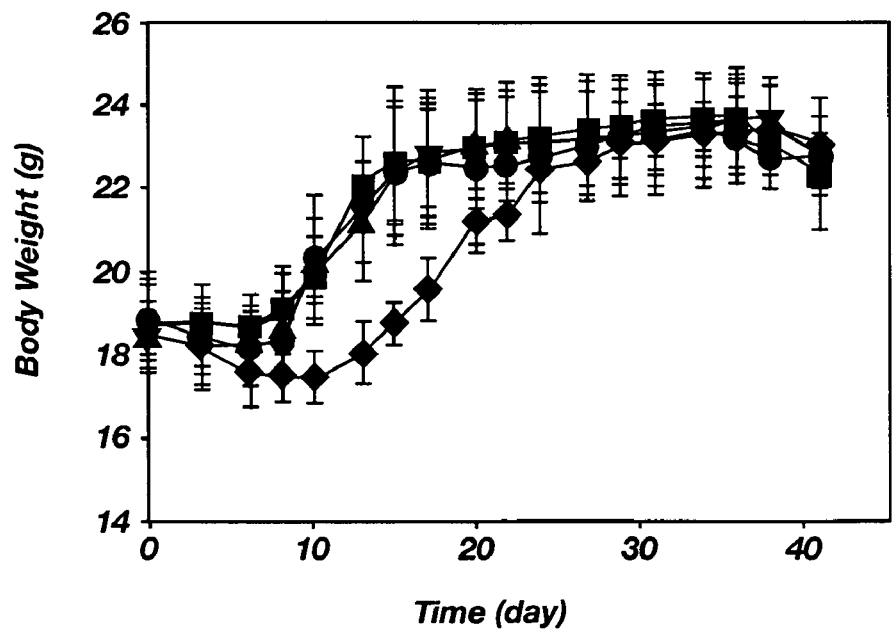

The MCF-7/DOX$^R$ xenografts in nude mice were used for the investigation of in vivo efficacy according to the procedure of Example 17. The tumor-bearing animals were treated by multiple intravenous injections on days 0, 3 and 6 (FIGS. 25A-B). Complete tumor growth regression and toxicity-induced death were not observed in all experimental groups. However, the tumor growth in mice treated by PHSM/f was inhibited and the size was reduced for 2 weeks after the third injection. The tumor volume in mice treated by PHSM/f (P<0.05 compared with free DOX) was approximately 2.7 times smaller than those treated with free DOX or PHIM and approximately 1.9 times smaller than those treated with PHSM after 6 weeks. These results indicate that the folate-mediated endocytosis pathway of PHSM/f enhances the regression of tumors and is more efficient for MDR tumor chemotherapy than PHSM. However, the tumor regression efficacy in PHIM/f was not significant because some folate conjugates may recycle back to the surface before drug unloading. In addition, slow or limited drug release from PHIM may associate with drug sequestration in acidic organelles in MDR cells. The active internalization, enhanced drug release rate and endosomal escaping activity justify the efficacy of PHSM/f.

Free DOX administration exhibited more weight loss in mice than the groups treated by any micelles (FIG. 25B), demonstrating less toxicity of DOX that was carried by micelles.

EXAMPLE 19

Growth Inhibition of Human Non-Small Lung NCI—H358 Carcinoma Xenografts

In this example, the procedure of Example 17 was carried except that the cells injected into the mice were human non-small lung carcinoma (NCI-H358) cells, and in vivo antitumor studies were performed 1-2 weeks (tumor volume 40-70 mm$^3$) after inoculation.

Figure 26A:
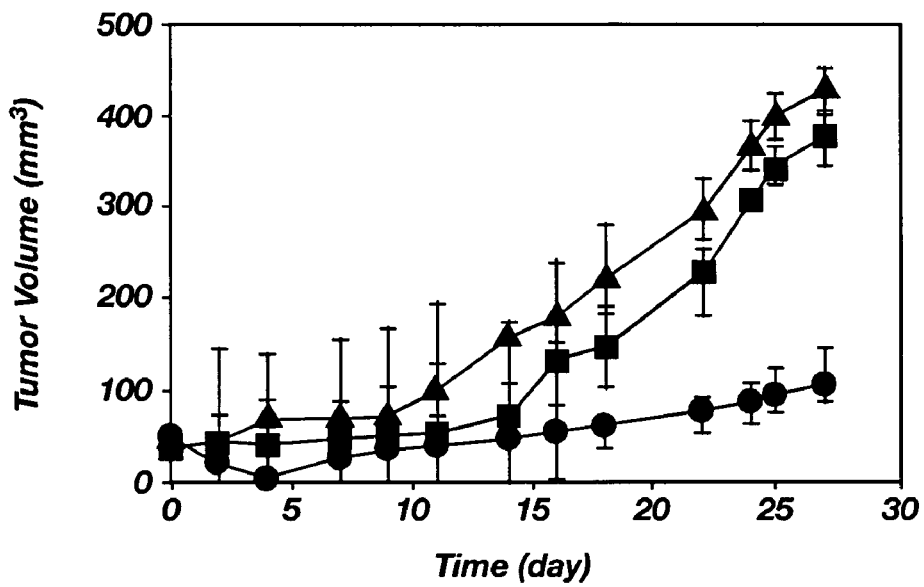
FIGS. 26A-B show in vivo tumor volume change (FIG. 26A) and body weight change (FIG. 26B) of human lung NCI—H358 carcinoma xenografts in BALB/c nude mice injected intravenously with 10 mg/kg DOX equivalent dose: mixed micelles of polyHis-b-PEG-folate and PLLA-b-PEG-folate at a 75:25 weight ratio (●), pLLA-b-PEG-folate micelles (■), and free DOX (▲); values are means±the standard deviation.
Figure 26B:
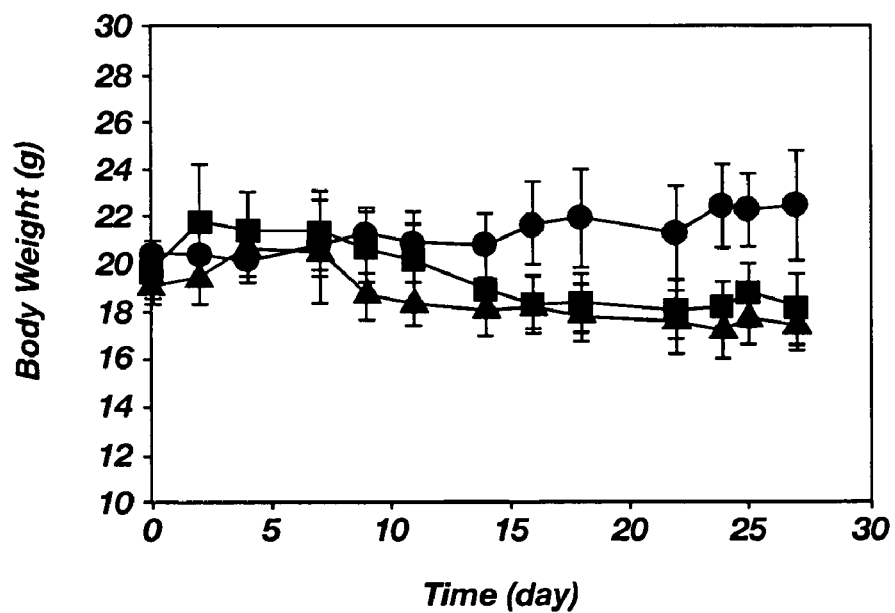

In vivo efficacy of PHSM/f was demonstrated with human non-small lung NCI-H358 carcinoma xenografts, which have characteristics of a fast growing and an intrinsic resistance to anticancer drugs. The in vivo results are presented in FIG. 26A and clearly demonstrate that the PHSM micelles are superior in tumor suppression as compared to PHIM and free DOX. After a single intravenous injection (day; 0) of the PHSM/f, tumor volume was reduced to minimal detectable size in 4 days. After 3 weeks, the tumor volume of mice treated by PHSM/f (P<0.05 compared with free DOX) was approximately 4.3 or 3.8 times smaller than those compared to free DOX or PHIM/f. No significant change in the weight was observed (FIG. 26B).

The invention claimed is:

1. A method for treating a warm-blooded animal with a drug comprising:
   (a) mixing the drug with a pH-sensitive mixed polymeric micelle composition comprising (i) poly(L-histidine)-poly (ethylene glycol) block copolymer and poly(L-lactic acid)-poly (ethylene glycol) block copolymer, (ii) poly(L-histidine)-poly (ethylene glycol) block copolymer-folate and poly(L-lactic acid)-poly(ethylene glycol) block copolymer, (iii) poly(L-histidine)-poly (ethylene glycol) block copolymer and poly(L-lactic acid)-poly (ethylene glycol) block copolymer-folate, or (iv) poly(L-histidine)-poly(ethylene glycol) block copolymer-folate and poly(L-lactic acid)-poly(ethylene glycol) block copolymer-folate, to result in a drug-loaded mixed micelle composition; and
   (b) administering the drug-loaded mixed micelle composition to the animal such that the drug-loaded mixed micelle composition is systemically circulated in the animal, wherein the drug-loaded mixed micelle composition is stable in blood and releases the drug in acidic conditions.

2. The method of claim 1 wherein the drug is hydrophobic.

3. The method of claim 1 wherein the drug is an anticancer drug.

4. The method of claim 1 wherein the drug comprises adriamycin.

5. The method of claim 1 wherein the pH-sensitive mixed polymeric micelle composition comprises about 60-90% by weight of poly(L-histidine)-poly(ethylene glycol) block copolymer or poly(L-histidine)-poly(ethylene glycol) block copolymer-folate and about 10-40% by weight of poly(L-lactic acid)-poly(ethylene glycol) block copolymer or poly (L-lactic acid)-poly(ethylene glycol) block copolymer-folate.

6. The method of claim 5 wherein the pH-sensitive mixed polymeric micelle composition comprises about 75% by weight of poly(L-histidine)-poly(ethylene glycol) block copolymer or poly(L-histidine)-poly (ethylene glycol) block copolymer-folate and about 25% by weight of poly(L-lactic acid) poly(ethylene glycol) block copolymer or poly(L-lactic acid)-poly (ethylene glycol) block copolymer-folate.

7. The method of claim 1 wherein the warm-blooded animal is a human.

8. A method for treating multidrug resistance in a warm-blooded animal comprising administering into the systemic circulation of the animal a drug-loaded mixed micelle composition comprising a mixture of a hydrophobic anticancer drug and pH-sensitive mixed polymeric micelles comprising (i) poly(L-histidine)-poly(ethylene glycol) block copolymer and poly(L-lactic acid)-poly(ethylene glycol) block copolymer, (ii) poly(L-histidine)-poly(ethylene glycol) block copolymer-folate and poly(L-lactic acid)-poly(ethylene glycol) block copolymer, (iii) poly(L-histidine)-poly(ethylene glycol) block copolymer and poly(L-lactic acid)-poly(ethylene glycol) block copolymer-folate, or (iv) poly(L-histidine)-poly(ethylene glycol) block copolymer-folate and poly(L-lactic acid)-poly (ethylene glycol) block copolymer-folate.

9. The method of claim 8 wherein the hydrophobic anticancer drug comprises adriamycin.

10. A method for treating a warm-blooded animal with a drug comprising:

(a) mixing the drug with a pH-sensitive mixed polymeric micelle composition comprising (i) poly(L-histidine)-poly (ethylene glycol) block copolymer or poly(L-histidine)-poly (ethylene glycol) block copolymer-targeting moiety and (ii) an amphiphilic polymer or amphiphilic polymer-targeting moiety, to result in a drug-loaded mixed micelle composition; and (b) administering the drug-loaded mixed micelle composition to the animal such that the drug-loaded mixed micelle composition is systemically circulated in the animal, wherein the drug-loaded mixed micelle composition is stable in blood and releases the drug in acidic conditions.

11. The method of claim 10 wherein the targeting moiety is folate.

12. The method of claim 10 wherein the amphiphilic polymer comprises poly(L-lactic acid)-poly(ethylene glycol) block copolymer.

13. A method for treating a warm-blooded animal with a drug comprising:

(a) mixing the drug with a ph-sensitive mixed polymeric micelle composition, wherein the pH-sensitive mixed polymeric micelle composition comprises poly(L-histidine) poly(ethylene glycol) block copolymer and an amphiphilic polymer selected from the group consisting of poly(L-lactic acid)-poly(ethylene glycol) block copolymer, poly(DL-lactic-co-glycolic acid), poly(ethylene oxide)-poly(propylene oxide)-poly(ethylene oxide) block copolymer, and mixtures thereof, to result in a drug-loaded mixed micelle composition wherein the drug-loaded mixed micelle composition is stable in blood and releases the drug in acidic conditions; and (b) administering the drug-loaded mixed micelle composition to the animal such that the drug-loaded mixed micelle composition is systemically circulated in the animal.

14. The method of claim 13 wherein the warm-blooded animal is a human.

15. The method of claim 13 wherein the drug is an anti-cancer drug.

16. The method of claim 13 wherein the poly(L-histidine)-poly(ethylene glycol) block copolymer, or the amphiphilic polymer, or both the poly(L-histidine)-poly (ethylene glycol) block copolymer and the amphiphilic polymer are covalently coupled to a targeting moiety.

17. The method of claim 16 wherein the targeting moiety comprises folate.

18. The method of claim 8 wherein the pH-sensitive mixed polymeric micelles comprise about 60-90% by weight of poly(L-histidine)-poly(ethylene glycol) block copolymer or poly(L-histidine)-poly(ethylene glycol) block copolymer-folate and about 10-40% by weight of poly(L-lactic acid)-poly(ethylene glycol) block copolymer or poly(L-lactic acid)-poly(ethylene glycol) block copolymer-folate.

19. The method of claim 10 wherein the amphiphilic polymer comprises poly(DL-lactic-co-glycolic acid).

20. The method of claim 10 wherein the amphiphilic polymer comprises an ABA block copolymer.

21. The method of claim 20 wherein the ABA block copolymer comprises a poly(ethylene oxide)-poly(propylene oxide)-poly(ethylene oxide) block copolymer.

* * * * *

UNITED STATES PATENT AND TRADEMARK OFFICE
CERTIFICATE OF CORRECTION

PATENT NO. : 7,659,314 B2 Page 1 of 1
APPLICATION NO. : 10/846487
DATED : February 9, 2010
INVENTOR(S) : You Han Bae et al.

It is certified that error appears in the above-identified patent and that said Letters Patent is hereby corrected as shown below:

Column 3, lines 61-64, "N-carbobenzoxy-$N^{im}$-dinitrophenyl-L-histidine" should read --$N^{\alpha}$-carbobenzoxy-$N^{im}$-dinitrophenyl-L-histidine--.

Column 12, line 24, "NO-CBZ-L-histidine" should read --$N^{\alpha}$-CBZ-L-histidine--.

Column 12, line 36, "Na-CBZ-L-histidine" should read --$N^{\alpha}$-CBZ-L-histidine--.

Column 12, lines 46-47, "NW-CBZ-$N^{im}$-DNP-L-histidine" should read --$N^{\alpha}$-CBZ-$N^{im}$-DNP-L-histidine--.

Column 12, line 49, "Na-CBZ-$N^{im}$-DNP-L-histidine" should read --$N^{\alpha}$-CBZ-$N^{im}$-DNP-L-histidine--.

Column 13, line 49, "NCA.HCl" should read --NCA·HCl--.

Column 13, line 52, "Nu-CBZ-$N^{im}$-DNP-L-histidine NCA.HCl" should read --$N^{\alpha}$-CBZ-$N^{im}$-DNP-L-histidine NCA·HCl--.

Column 15, line 51, "pKb" should read --$pK_b$--.

Column 26, line 40, "doxorubicin-PLURONIC®" should read --doxorubicin-PLURONIC®--.

Column 26, line 46, "PLURONIC®" should read --PLURONIC®--.

Column 30, lines 26-27, "doxorubicin.HCl" should read --doxorubicin·HCl--.

Column 33, line 21, "ph-sensitive" should read --pH-sensitive--.

Signed and Sealed this

Tenth Day of August, 2010

David J. Kappos
*Director of the United States Patent and Trademark Office*